(12) United States Patent
Ghosh et al.

(10) Patent No.: US 11,376,261 B2
(45) Date of Patent: Jul. 5, 2022

(54) METHODS FOR DIAGNOSING AND MANAGING TREATMENT OF ATOPIC DERMATITIS

(71) Applicants: University of Cincinnati, Cincinnati, OH (US); Cincinnati Children's Hospital Medical Center, Cincinnati, OH (US)

(72) Inventors: Debajyoti Ghosh, Cincinnati, OH (US); Tesfaye Mersha, Cincinnati, OH (US); Jonathan A. Bernstein, Cincinnati, OH (US)

(73) Assignees: University of Cincinnati, Cincinnati, OH (US); Children's Hospital Medical Center, Cincinnati, OH (US)

( * ) Notice: Subject to any disclaimer, the term of this patent is extended or adjusted under 35 U.S.C. 154(b) by 252 days.

(21) Appl. No.: 16/224,143

(22) Filed: Dec. 18, 2018

(65) Prior Publication Data
US 2019/0183904 A1    Jun. 20, 2019

Related U.S. Application Data

(60) Provisional application No. 62/599,903, filed on Dec. 18, 2017.

(51) Int. Cl.
| | |
|---|---|
| *C12Q 1/6883* | (2018.01) |
| *A61K 31/56* | (2006.01) |
| *G16B 30/10* | (2019.01) |
| *A61P 17/00* | (2006.01) |
| *C12Q 1/686* | (2018.01) |

(Continued)

(52) U.S. Cl.
CPC .............. *A61K 31/56* (2013.01); *A61P 17/00* (2018.01); *C12Q 1/686* (2013.01); *C12Q 1/6806* (2013.01); *C12Q 1/6883* (2013.01); *G16B 20/00* (2019.02); *G16B 30/10* (2019.02); *G16B 40/20* (2019.02); *G16B 40/30* (2019.02); *C12Q 2600/106* (2013.01); *C12Q 2600/112* (2013.01); *C12Q 2600/158* (2013.01); *G16B 25/00* (2019.02)

(58) Field of Classification Search
CPC ......................... C12Q 1/6883; C12Q 2600/158
See application file for complete search history.

(56) References Cited

PUBLICATIONS

Hamilton, J. D. et al. J. Allergy Clin. Immunol. 134(6):1293. (Year: 2014).*

(Continued)

*Primary Examiner* — Diana B Johannsen
(74) *Attorney, Agent, or Firm* — Dinsmore & Shohl LLP

(57) ABSTRACT

Provided herein is a method of diagnosing and treating a subject suffering from atopic dermatitis (AD), the method comprising: (a) obtaining a skin biopsy from a subject suspected of suffering from AD; (b) determining a level of RNA expression in the skin biopsy of genes selected from the 89ADGES gene panel; (c) comparing the determined level of RNA expression of the selected genes to the level of RNA expression of the selected genes in a reference sample comprising RNA expression products from normal healthy skin cells; (d) diagnosing the subject as suffering from AD when specific genes are up-regulated compared to the reference sample and when specific genes are down-regulated compared to the reference sample; and (e) treating the subject with a therapy effective for the treatment of AD. Methods of managing treatment of a subject suffering from AD are also provided.

9 Claims, 5 Drawing Sheets

Specification includes a Sequence Listing.

(51) Int. Cl.
*C12Q 1/6806* (2018.01)
*G16B 40/20* (2019.01)
*G16B 40/30* (2019.01)
*G16B 20/00* (2019.01)
*G16B 25/00* (2019.01)

(56) References Cited

PUBLICATIONS

Jensen, J.M. et al. Allergy 67:413. (Year: 2011).*
Wollenberg, A. & Feichtner, K. Allergy 68:1509. (Year: 2013).*
Debajyoti Ghosh et al, "Multiple Transcriptome Data Analysis Reveals Biologically Relevant Atopic Dermatitis Signature Genes and Pathways"; PLOS ONE; DOI:10.1371;journal.pone.0144316, Dec. 30, 2015, 1-23.

* cited by examiner

| Cluster Summary | | | | | |
|---|---|---|---|---|---|
| Cluster | Number of Members | Most Representative Variable | Cluster Proportion of Variation Explained | Total Proportion of Variation Explained | .2 .4 .6 .8 |
| 1 | 17 | NCAPG | 0.807 | 0.225 | |
| 4 | 12 | LOR | 0.755 | 0.149 | |
| 3 | 7 | APOBEC3A | 0.744 | 0.065 | |
| 6 | 6 | BTC_1 | 0.822 | 0.081 | |
| 2 | 5 | RNASE7_3 | 0.857 | 0.07 | |
| 8 | 5 | BTC_2 | 0.786 | 0.064 | |
| 7 | 5 | AQP9 | 0.698 | 0.057 | |
| 5 | 4 | GALNT6 | 0.751 | 0.049 | |

Proportion of variation explained by clustering: 0.781

Figure 3

| Cluster Summary | | | | | |
|---|---|---|---|---|---|
| Cluster | Number of Members | Most Representative Variable | Cluster Proportion of Variation Explained | Total Proportion of Variation Explained | .2 .4 .6 .8 |
| 1 | 16 | RNASE7_1 | 0.81 | 0.209 | |
| 4 | 12 | LOR | 0.755 | 0.146 | |
| 3 | 8 | APOBEC3A | 0.716 | 0.092 | |
| 7 | 6 | BTC_1 | 0.822 | 0.08 | |
| 2 | 5 | RNASE7_3 | 0.857 | 0.069 | |
| 5 | 6 | AQP9 | 0.703 | 0.068 | |
| 8 | 5 | BTC_2 | 0.786 | 0.063 | |
| 6 | 4 | GALNT6 | 0.81 | 0.052 | |

Proportion of variation explained by clustering: 0.78

Figure 4

| | ECZEMA55 | Eczema/Normal | Betamethasone (Post/Pre) | Pimecrolimus (Post/Pre) | Dupilumab (Post/Pre) |
|---|---|---|---|---|---|
| 1 | SERPINB4 | 6.277 | -5.240 | -1.811 | -5.850 |
| 2 | AKR1B10 | 5.545 | -1.908 | -0.531 | -3.180 |
| 3 | SERPINB3 | 4.647 | -3.719 | -1.309 | -3.520 |
| 4 | S100A7 | 4.368 | -2.404 | -0.408 | -0.449 |
| 5 | DEFB4A | 4.246 | -4.280 | -1.356 | -2.400 |
| 6 | RRM2 | 4.097 | -1.556 | -0.757 | -2.330 |
| 7 | CCL18 | 4.005 | -2.086 | 0.108 | -2.720 |
| 8 | PI3 | 4.004 | -4.419 | -1.206 | -3.370 |
| 9 | COL6A6 | 3.903 | -1.836 | -0.561 | -2.750 |
| 10 | KRT16 | 3.847 | -3.421 | -1.091 | -1.820 |
| 11 | S100A8 | 3.444 | -1.813 | -0.583 | -1.430 |
| 12 | RGS1 | 3.417 | -1.998 | -1.161 | -1.840 |
| 13 | CCL22 | 3.351 | -2.439 | -1.144 | -1.670 |
| 14 | NCAPG | 2.956 | -0.950 | -0.383 | -1.250 |
| 15 | TMPRSS4 | 2.932 | -2.438 | -0.656 | -3.330 |
| 16 | KYNU | 2.918 | -1.155 | -0.445 | -2.040 |
| 17 | SELE | 2.446 | -2.276 | -1.010 | -3.440 |
| 18 | GALNT6 | 2.367 | -1.347 | -0.670 | -1.520 |
| 19 | PGF | 2.326 | -1.170 | -0.506 | -1.520 |
| 20 | CCL17 | 2.278 | -1.188 | -0.745 | -3.320 |
| 21 | APOBEC3A | 2.247 | -2.406 | -1.202 | -4.420 |
| 22 | TYMP | 2.098 | -1.686 | -1.043 | -1.150 |
| 23 | IL27RA | 2.044 | -1.489 | -0.689 | -1.160 |
| 24 | GPR171 | 2.019 | -0.590 | -0.216 | -1.710 |
| 25 | GZMB | 1.983 | -2.270 | -1.605 | -3.560 |
| 26 | TACC3 | 1.903 | -0.669 | -0.329 | -0.440 |
| 27 | CD1B | 1.709 | -2.029 | -0.854 | -3.820 |
| 28 | CHP2 | -1.489 | 1.118 | 0.747 | 1.270 |
| 29 | DIO2 | -1.703 | -0.169 | 0.202 | -2.060 |
| 30 | OMD | -1.801 | 0.343 | 0.352 | 2.160 |
| 31 | HSD11B1 | -1.920 | 1.728 | 0.040 | -0.422 |
| 32 | GPD1 | -1.940 | 1.365 | -0.313 | 1.660 |
| 33 | HPGDS | -1.980 | 0.195 | 0.351 | 1.180 |
| 34 | FAR2 | -1.998 | 1.154 | 0.176 | -0.019 |
| 35 | AQP9 | -2.067 | 1.090 | 0.490 | 0.293 |
| 36 | PSG7 | -2.123 | 0.000 | 0.188 | 0.287 |
| 37 | DKK2 | -2.160 | -0.101 | 0.159 | 1.290 |
| 38 | LGR5 | -2.164 | 0.356 | 0.206 | 3.030 |
| 39 | ARG1 | -2.191 | 0.534 | 0.669 | -0.774 |
| 40 | OGN | -2.291 | 0.697 | 0.592 | 1.200 |
| 41 | CTSV | -2.292 | 1.148 | 0.752 | 0.283 |
| 42 | CARD18 | -2.307 | 0.850 | 0.272 | -0.665 |
| 43 | FABP7 | -2.346 | 2.294 | 0.856 | 0.509 |
| 44 | MSMB | -2.452 | 1.243 | 1.252 | 1.390 |
| 45 | LOR | -2.494 | 1.621 | 1.160 | 0.885 |
| 46 | SLC46A2 | -2.546 | 1.532 | 1.035 | 2.280 |
| 47 | GAL | -2.638 | 2.946 | 0.560 | 0.823 |
| 48 | RNASE7 | -2.649 | 0.040 | 0.507 | -0.454 |
| 49 | IL37 | -2.739 | 3.053 | 1.790 | 1.790 |
| 50 | PSORS1C2 | -2.861 | 1.157 | 0.512 | 0.640 |
| 51 | CRCT1 | -3.069 | 0.376 | 0.410 | -0.828 |
| 52 | FADS1 | -3.115 | 0.980 | 0.116 | -0.497 |
| 53 | C1orf68 | -3.139 | 1.402 | 0.870 | 0.898 |
| 54 | BTC | -3.220 | 1.795 | 0.920 | 0.758 |
| 55 | LCE2B | -3.598 | 1.456 | 1.031 | 0.308 |

Figure 6

METHODS FOR DIAGNOSING AND MANAGING TREATMENT OF ATOPIC DERMATITIS

CROSS REFERENCE TO RELATED APPLICATIONS

This application claims priority to U.S. Provisional Application Ser. No. 62/599,903, filed Dec. 18, 2017, which application is hereby incorporated by reference in its entirety.

FEDERALLY SPONSORED RESEARCH OR DEVELOPMENT

This invention was made with Government support under K01 HL103165 awarded by the National Institute of Health. The Government has certain rights in the invention.

TECHNICAL FIELD

This disclosure relates to the field of molecular diagnosis and treatment. More specifically, this disclosure relates to molecular methods of diagnosing and managing treatment of atopic dermatitis.

BACKGROUND

Atopic dermatitis (AD; eczema) is a periodically relapsing, chronic inflammatory skin disease characterized by itch and recurrent eczematous lesions. Although it affects two out of ten children, it is also quite prevalent in adults. In spite of its high clinical significance, the current strategy for diagnosis of AD depends on obtaining the patient's family history and visual assessment of the skin, as there is no specific laboratory test clinically available for confirming a diagnosis or assessing treatment outcomes. Moreover, different severity scoring scales such as Eczema Area and Severity Index (EASI), Severity Scoring of Atopic Dermatitis (SCORAD), patient-oriented SCORAD (PO-SCORAD), Patient-Oriented Eczema Measure (POEM) etc. are used by different clinicians, requiring more harmonized outcome measures for clinical trials. The current diagnosis and treatment-response monitoring of AD is therefore time-consuming, based entirely on personal experience of the clinicians, and therefore subject to human error.

Gene expression profiling data (either generated by individual group or obtained from public repositories) serve as a tool to predict drug responsiveness for many complex diseases like cancers and several autoimmune and inflammatory diseases. This approach has also been successfully used in diagnosis of eosinophilic esophagitis (another inflammatory disease like AD), for which no molecular diagnostic tool was previously available. These genome-wide expression studies utilized microarray or RNAseq techniques to identify differentially regulated genes (DEGs) for diagnosis and molecular profiling of the disease condition and to evaluate treatment outcomes. The expression of selected/prioritized DEGs can be readily quantified and compared between disease or treatment states for quick, accurate, and cost-effective diagnosis.

AD is currently treated using drugs (such as topical therapies) or narrow-band UVB. Approximately 20% of AD patients have moderate-to-severe disease, which is either refractory or only partially responsive to the available topical therapies. Emerging clinical trials and multiple treatment options strongly underscore the necessity of a generalized gene panel for accurately monitoring treatment options. Multi-origin gene expression data in the public domain are invaluable resources for biomedical research particularly related to drug repositioning, drug discovery, and treatment response monitoring. In the case of AD, several microarray-based gene expression datasets have been deposited by independent investigators, which permit the identification of differentially expressed genes in AD disease state compared to normal skin from punch biopsy samples.

A need exists for improved molecular diagnosis and treatment monitoring tools for the benefit of patients suffering from atopic dermatitis.

SUMMARY

Consistent with these findings, the present inventors have designed a gene panel for definitive molecular diagnosis of AD and monitoring of treatment outcomes of AD patients. Accordingly, provided herein is a method for diagnosing and treating a subject suffering from atopic dermatitis (AD), the method comprising: (a) obtaining a skin biopsy from a subject suspected of suffering from AD; (b) determining a level of RNA expression in the skin biopsy of genes selected from the group consisting of SERPINB4, AKR1B10, SERPINB3, S100A7, DEFB4A, RRM2, CCL18, PI3, COL6A6, KRT16, S100A8, RGS1, CCL22, NCAPG, TMPRSS4, KYNU, KRT6, SELE, GALNT6, PGF, CCL17, APOBEC3A, TYMP, IL27RA, GPR171, GZMB, EHBP1L1, TACC3, CBLC, CD1B, IGL, LCE2B, CDSN, BTC, C1orf46, C1orf68, FADS1, CRCT1, ASPRV1, PSOR1C2, SERPINB7, IL1F7, RNASE7, GAL, SLC46A2, POF1B, LOR, SLURP1, MSMB, CST6, HBB, ELMOD1, CORIN, FABP7, SCGB2A1, CARD18, CTSL2, OGN, LOC100130476, GREM1, GPLD1, HBA, ARG1, ANXA9, LGR5, DKK2, KLK5, LYVE1, PSG7, C15orf48, AQP9, FAR2, HPGDS, CPA3, GPD1, SLIT2, HSD11B1, IGJ, ARHGAP18, EREG, CLDN23, SFRP2, FLG, MUC15, SCEL, OMD, LOX, DIO2, and CHP2; (c) comparing said determined level of RNA expression of the selected genes to the level of expression of the selected genes in a reference sample comprising RNA expression products from normal healthy skin cells; (d) diagnosing the subject as suffering from AD when SERPINB4, AKR1B10, SERPINB3, S100A7, DEFB4A, RRM2, CCL18, PI3, COL6A6, KRT16, S100A8, RGS1, CCL22, NCAPG, TMPRSS4, KYNU, KRT6, SELE, GALNT6, PGF, CCL17, APOBEC3A, TYMP, IL27RA, GPR171, GZMB, EHBP1L1, T4CC3, CBLC, CD1B, and IGL are up-regulated compared to the reference sample and when LCE2B, CDSN, BTC, C1orf46, C1orf68, FADS1, CRCT1, ASPRV1, PSOR1C2, SERPINB7, IL1F7, RNASE7, GAL, SLC46A2, POF1B, LOR, SLURP1, MSMB, CST6, HBB, ELMOD1, CORIN, FABP7, SCGB2A1, CARD18, CTSL2, OGN, LOC100130476, GREM1 GPLD1, HBA, ARG1, ANXA9, LGR5, DKK2, KLK5, LYVE1, PSG7, C15orf48, AQP9, FAR2, HPGDS, CPA3, GPD1, SLIT2, HSD11B1, IGJ, ARHGAP18, EREG, CLDN23, SFRP2, FLG, MUC15, SCEL, OMD, LOX DIO2, and CHP2 are down-regulated compared to the reference sample; and (e) treating the subject with one or more therapeutic agents selected from the group consisting of corticosteroids, betamethasone, tacrolimus, pimecrolimus, narrow-band UVB, PDE4 inhibitors, tofacitinib, dupilumab, and nemolizumab.

In another embodiment, a method of diagnosing and treating a subject suffering from AD is provided, the method comprising: (a) obtaining a skin biopsy from a subject suspected of suffering from AD; (b) generating a skin biopsy transcriptional profile comprising RNA expression levels of a plurality of genes selected from the group consisting of SERPINB4, AKR1B10, SERPINB3, S100A7, DEFB4A, RRM2, CCL18, PI3, COL6A6, KRT16, S100A8, RGS1, CCL22, NCAPG, TMPRSS4, KYNU, KRT6, SELE, GALNT6, PGF, CCL17, APOBEC3A, TYMP, IL27RA, GPR171, GZMB, EHBP1L1, T4CC3, CBLC, CD1B, IGL, LCE2B, CDSN, BTC, C1orf46, C1orf68, FADS, CRCT1, ASPRV1, PSOR1C2, SERPINB7, IL1F7, RNASE7, GAL, SLC46A2, POF1B, LOR, SLURP1, MSMB, CST6, HBB, ELMOD1, CORIN, FABP7, SCGB2A1, CARD18, CTSL2, OGN, LOC100130476, GREM1, GPLD1, HBA, ARG1, ANXA9, LGR5, DKK2, KLK5, LYVE1, PSG7, C15orf48, AQP9, FAR2, HPGDS, CPA3, GPD1, SLIT2, HSD11B1, IGJ, ARHGAP18, EREG, CLDN23, SFRP2, FLG, MUC15, SCEL, OMD, LOX, DIO2, and CHP2; (c) comparing the skin biopsy transcriptional profile to an AD signature transcriptional profile of the selected genes; (d) diagnosing the subject as suffering from AD when the skin biopsy transcriptional profile and the AD signature transcriptional profile are at least 25% concordant; and (e) treating the subject with one or more therapeutic agents selected from the group consisting of corticosteroids, betamethasone, tacrolimus, pimecrolimus, narrow-band UVB, PDE4 inhibitors, tofacitinib, dupilumab, and nemolizumab.

In another embodiment, a method of managing treatment of a subject suffering from atopic dermatitis (AD) is provided, the method comprising: (a) obtaining a pre-treatment skin biopsy from the subject; (b) generating a pre-treatment transcriptional profile comprising RNA expression levels of at least 4 genes selected from the group consisting of SERPINB4, AKR1B10, SERPINB3, S100A7, DEFB4A, RRM2, CCL18, PI3, COL6A6, KRT16, S100A8, RGS1, CCL22, NCAPG, TMPRSS4, KYNU, SELE, GALNT6, PGF, CCL17, APOBEC3A, TYMP, IL27RA, GPR171, GZMB, TACC3, CD1B, CHP2, DIO2, OMD, HSD11B1, GPD1, HPGDS, FAR2, AQP9, PSG7, DKK2, LGR5, ARG1, OGN, CTSV, CARD18, FABP7, MSMB, LOR, SCL46A2, GAL, RNASE7, IL37, PSOR1C2, CRCT1, FADS1, C1orf68, BTC, and LCE2B; (c) administering to the subject a therapeutic agent; (d) obtaining a post-treatment skin biopsy from the subject; (e) generating a post-treatment transcriptional profile comprising RNA expression levels of the selected genes; (f) comparing the post-treatment transcriptional profile to the pre-treatment transcriptional profile of the selected genes to determine up-regulation and/or down-regulation of expression of the selected genes in response to the therapeutic agent; and (g) administering one or more additional doses of the therapeutic agent to the subject when the comparison of the post-treatment transcriptional profile and the pre-treatment transcriptional profile indicate the RNA expression levels of the selected genes in the subject are up-regulated and/or down-regulated in a manner directionally opposite to RNA expression level changes observed in an AD disease state compared to normal, healthy skin.

These and other objects, features, embodiments, and advantages will become apparent to those of ordinary skill in the art from a reading of the following detailed description and the appended claims.

BRIEF DESCRIPTION OF THE DRAWINGS

FIG. 3 shows the number of ECZEMA55 treatments-responsive genes (variables) in each cluster, most representative gene variable in the cluster along with Cluster Proportion of Variation Explained and Total Proportion of Variation Explained. Dupilumab-response can be grouped into 8 clusters. They are arranged by the number of member genes they contain.

FIG. 4 shows the ECZEMA55 treatments-responsive genes (variables) in each cluster along with the pre-treatment symptom score, most representative gene variable in the cluster along with Cluster Proportion of Variation Explained and Total Proportion of Variation Explained. Dupilumab-response can be grouped into 8 clusters. They are arranged by the number of member genes they contain.

FIG. 6 shows expression of members of the ECZEMA55 gene panel compared to normal skin. Expression changes due to different treatment options (betamethasone, pimecrolimus, and dupilumab) are shown. Note direction and magnitude of treatment-related expression change for each gene. Treatment inducing change in a direction opposite to that occurring in ECZEMA55 can drive treatment-associated health benefits.

DETAILED DESCRIPTION

Figure 1:
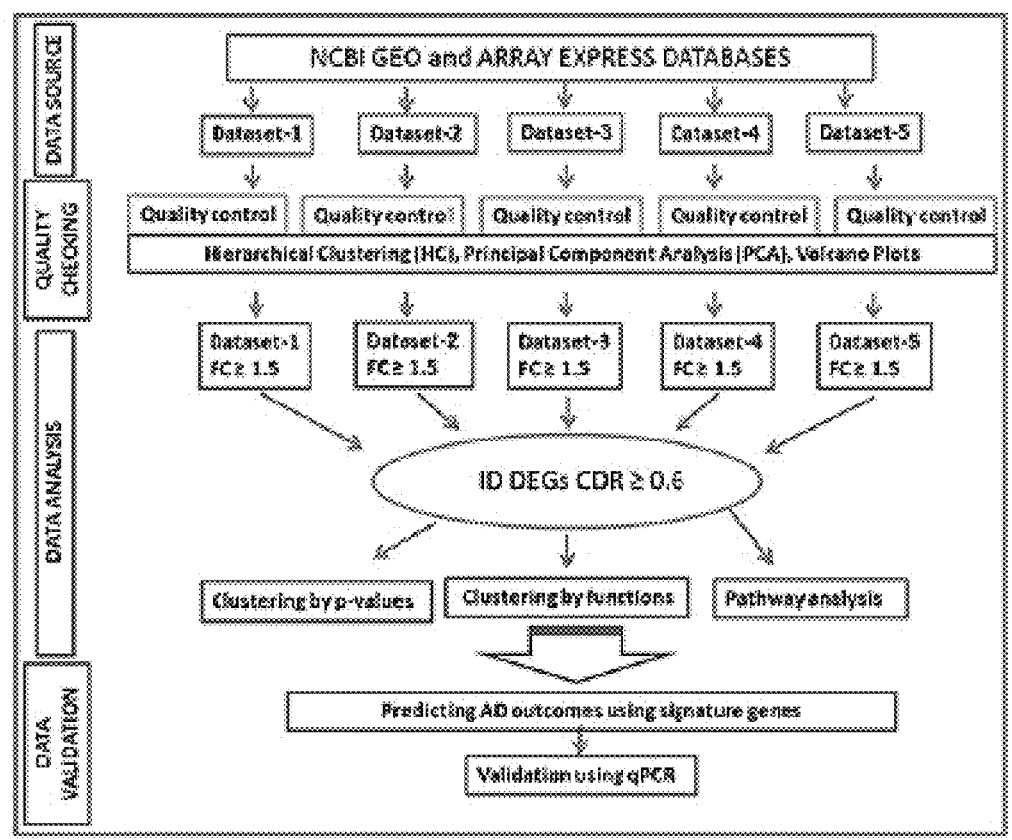
FIG. 1 shows a flow-chart analysis of methods of analyzing transcriptome data. Five datasets were normalized and quality checked using hierarchical cluster analysis (HCA) and principal component analysis (PCA). Differentially expressed genes (DEGs) were identified from each dataset. Genes differentially regulated between AD and non-AD controls in at least 3/5 datasets were ranged by fold change. Ingenuity support Vector Machine and discriminate analysis were used to discriminate and predict membership of AD patients from healthy controls.

The details of one or more embodiments of the presently-disclosed subject matter are set forth in this document. Modifications to embodiments described in this document, and other embodiments, will be evident to those of ordinary skill in the art after a study of the information provided herein.

While the following terms are believed to be well understood by one of ordinary skill in the art, definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, pH, size, concentration or percentage is meant to encompass variations of in some embodiments±20%, in some embodiments±10%, in some embodiments±5%, in some embodiments±1%, in some embodiments±0.5%, and in some embodiments±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

An "effective amount," as used herein, refers to an amount of a substance (e.g., a therapeutic compound and/or composition) that elicits a desired biological response. In some embodiments, an effective amount of a substance is an amount that is sufficient, when administered to a subject suffering from or susceptible to a disease, disorder, and/or condition, to treat, diagnose, prevent, and/or delay and/or alleviate one or more symptoms of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a formulation to treat a disease, disorder, and/or condition is the amount that alleviates, ameliorates, relieves, inhibits, prevents, delays onset of; reduces severity of and/or reduces incidence of one or more symptoms or features of the disease, disorder, and/or condition. Furthermore, an effective amount may be administered via a single dose or via multiple doses within a treatment regimen. In some embodiments, individual doses or compositions are considered to contain an effective amount when they contain an amount effective as a dose in the context of a treatment regimen. Those of ordinary skill in the art will appreciate that a dose or amount may be considered to be effective if it is or has been demonstrated to show statistically significant effectiveness when administered to a population of patients; a particular result need not be achieved in a particular individual patient in order for an amount to be considered to be effective as described herein.

The terms "treat," "treatment," and "treating," as used herein, refer to a method of alleviating or abrogating a disease, disorder, and/or symptoms thereof in a subject.

As used herein, a "subject" refers to a mammal. Optionally, a subject is a human or non-human primate. Optionally, the subject is selected from the group consisting of mouse, rat, rabbit, monkey, pig, and human. In a specific embodiment, the subject is a human.

"Concordant," as used herein, refers to the degree of identity between compared datasets, transcriptional profiles, or gene or RNA expression levels. In certain embodiments, concordant refers to at least 25%, at least 50%, at least 75%, at least 80%, at least 85%, at least 90%, at least 91%/i, at least 92%, at least 93%, at least 94%/i, at least 95%, at least 96%, at least 98%, at least 99%, or 100% identity.

Atopic dermatitis (AD), also known as eczema, is a periodically relapsing chronic inflammatory skin disease characterized by itchy, red, dry, scaly, and/or crusty skin lesions. Gene expression profiling data (either generated by individual group or obtained from public repositories) serve as a tool to predict drug responsiveness for many complex diseases like cancers and certain autoimmune and inflammatory diseases. This approach has also been successfully used in diagnosis of eosinophilic esophagitis. These genome-wide expression studies utilized microarray or RNAseq techniques to identify differentially regulated genes (DEGs) for diagnosis and molecular profiling of the disease condition and to evaluate treatment outcomes. The expression of selected/prioritized DEGs can be readily quantified and compared between disease or treatment states for quick, accurate and cost-effective diagnosis.

Multi-origin gene expression data that are in the public domain have been designated as invaluable resource for biomedical research particularly related to drug repositioning, drug discovery and treatment response monitoring. In the case of AD, several microarray-based gene expression datasets have been deposited by independent investigators that have allowed the identification of differentially expressed genes (DEGs) in the AD disease state, compared to normal skin from punch biopsy samples.

A set of 89 DEGs (89 DEGS) has been identified, wherein AD-affected skin samples and normal healthy control skin samples can be distinguished with 98% accuracy. The 89ADGES gene panel is useful in the diagnosis and subsequent treatment of AD.

In one embodiment, a method of diagnosing and treating a subject suffering from atopic dermatitis (AD) is provided, the method comprising: (a) obtaining a skin biopsy from a subject suspected of suffering from AD; (b) determining a level of RNA expression in the skin biopsy of genes selected from the group consisting of SERPINB4, AKR1B10, SERPINB3, S100A7, DEFB4A, RRM2, CCL18, PI3, COL6A6, KRT16, S100A8, RGS1, CCL22, NCAPG, TMPRSS4, KYNU, KRT6, SELE, GALNT6, PGF, CCL17, APOBEC3A, TYMP, IL27RA, GPR171, GZMB, EHBP1L1, TACC3, CBLC, CD1B, IGL, LCE2B, CDSN, BTC, C1orf46, C1orf68, FADS1, CRCT1, ASPRV1, PSOR1C2, SERPINB7, IL1F7, RNASE7, GAL, SLC46A2, POF1B, LOR, SLURP1, MSMB, CST6, HBB, ELMOD1, CORIN, FABP7, SCGB2A1, CARD18, CTSL2, OGN, LOC100130476, GREM1, GPLD1, HBA, ARG1, ANXA9, LGR5, DKK2, KLK5, LYVE1, PSG7, C15orf48, AQP9, FAR2, HPGDS, CPA3, GPD1, SLIT2, HSD11B1, IGJ, ARHGAP18, EREG, CLDN23, SFRP2, FLG, MUC15, SCEL, OMD, LOX DIO2, and CHP2 (i.e., 89ADGES gene panel) (c) comparing said determined level of RNA expression of the selected genes to the level of expression of the selected genes in a reference sample comprising RNA expression products from normal healthy skin cells; (d) diagnosing the subject as suffering from AD when SERPINB4, AKR1B10, SERPINB3, S100A7, DEFB4A, RRM2, CCL18, PI13, COL6A6, KRT16, S100A8, RGS1, CCL22, NCAPG, TMPRSS4, KYNU, KRT6, SELE, GALNT6, PGF, CCL17, APOBEC3A, TYMP, IL27RA, GPR171, GZMB, EHBP1L1, TACC3, CBLC, CD1B, and IGL are up-regulated compared to the reference sample and when LCE2B, CDSN, BTC, C1orf46, C1orf68, FADS1, CRCT1, ASPRV1, PSOR1C2, SERPINB7, IL1F7, RNASE7, GAL, SLC46A2, POF1B, LOR, SLURP1, MSMB, CST6, HBB, ELMOD1, CORIN, FABP7, SCGB2A1, CARD18, CTSL2, OGN, LOC100130476, GREM1, GPLD1, HBA, ARG1, ANXA9, LGR5, DKK2, KLK5, LYVE1, PSG7, C15orf48, AQP9, FAR2, HPGDS, CPA3, GPD1, SLIT2, HSD11B1, IGJ, ARHGAP18, EREG, CLDN23, SFRP2, FLG, MUC15, SCEL, OMD, LOX, DIO2, and CHP2 are down-regulated compared to the reference sample; and (e) treating the subject with one or more therapeutic agents selected from the group consisting of corticosteroids, betamethasone, tacrolimus, pimecrolimus, narrow-band UVB, PDE4 inhibitors, tofacitinib, dupilumab, and nemolizumab.

In embodiments, determining RNA expression levels comprises molecular methods selected from the group consisting of quantitative RT-PCR, microarray, and RNA-seq. Such methods are known in the art and within the purview of skilled practitioners in the field.

In embodiments, determining a level of RNA expression in the skin biopsy comprises: (a) isolating RNA from the skin biopsy; (b) using the isolated RNA to create cRNA; (c) labeling the cRNA with a fluorescent dye; and (d) hybridizing the labeled cRNA to a microarray.

In certain embodiments, RNA expression levels are determined for all 89 genes in the 89ADGES set of genes set forth in Table 3. In other embodiments, the transcriptional profile may comprise RNA expression data related to a subset of genes selected from 89ADGES. For example, in some embodiments, the transcriptional profile may comprise at least 5, at least 10, at least 15, at least 20, at least 25, at least 30, at least 35, at least 40, at least 45, at least 50, at least 55, at least 60, at least 65, at least 70, at least 75, at least 80, at least 85, at least 86, at least 87, or at least 88 genes selected from the 89ADGES set of genes.

In another embodiment, a method of diagnosing and treating a subject suffering from AD is provided, the method comprising: (a) obtaining a skin biopsy from a subject suspected of suffering from AD; (b) generating a skin biopsy transcriptional profile comprising RNA expression levels of a plurality of genes selected from the group consisting of SERPINB4, AKR1B10, SERPINB3, S100A7, DEFB4A, RRM2, CCL18, PI3, COL6A46, KRT16, S100A8, RGS1, CCL22, NCAPG, TMPRSS4, KYNU, KRT6, SELE, GALNT6, PGF, CCL17, APOBEC3A, TYMP, IL27RA, GPR171, GZMB, EHBP1L1, TACC3, CBLC, CD1B, IGL, LCE2B, CDSN, BTC, C1orf46, C1orf68, FADS1, CRCT1, ASPRV1, PSOR1C2, SERPINB7, IL1F7, RNASE7, GAL, SLC46A2, POF1B, LOR, SLURP1, MSMB, CST6, HBB, ELMOD1, CORIN, FABP7, SCGB2A1, CARD18, CTSL2, OGN, LOC100130476, GREM1, GPLD1, HBA, ARG1, ANXA9, LGR5, DKK2, KLK5, LYVE1, PSG7, C15orf48, AQP9, FAR2, HPGDS, CPA3, GPD1, SLIT2, HSD11B1, IGJ, ARHGAP18, EREG, CLDN23, SFRP2, FLG, MUC15, SCEL, OMD, LOX, DIO2, and CHP2; (c) comparing the skin biopsy transcriptional profile to an AD signature transcriptional profile of the selected genes; (d) diagnosing the subject as suffering from AD when the skin biopsy transcriptional profile and the AD signature transcriptional profile are at least 25% concordant; and (e) treating the subject with one or more therapeutic agents selected from the group consisting of corticosteroids, betamethasone, tacrolimus, pimecrolimus, narrow-band UVB, PDE4 inhibitors, tofacitinib, dupilumab, and nemolizumab.

In certain embodiments, the transcriptional profiles comprise RNA expression levels determined for all 89 genes in the 89ADGES set of genes set forth in Table 3. In other embodiments, the transcriptional profiles may comprise data related to a subset of genes selected from 89ADGES. For example, in some embodiments, the transcriptional profile may comprise data for at least 5, at least 10, at least 15, at least 20, at least 25, at least 30, at least 35, at least 40, at least 45, at least 50, at least 55, at least 60, at least 65, at least 70, at least 75, at least 80, at least 85, at least 86, at least 87, or at least 88 genes selected from the 89ADGES set of genes. In embodiments, the AD signature transcriptional profile comprises the transcriptional profile and RNA expression levels set forth in Table 3.

In embodiments, the step of generating a skin biopsy transcriptional profile comprises: (a) determining RNA expression levels in the skin biopsy for the selected genes; and (b) comparing the RNA expression levels of the selected genes in the skin biopsy to control RNA expression levels from normal healthy skin cells to generate the skin biopsy transcriptional profile.

In embodiments, determining RNA expression levels comprises molecular methods selected from the group consisting of quantitative RT-PCR, microarray, and RNA-seq. Such methods are known in the art and within the purview of skilled pracitioners in the field.

In a specific embodiment, determining RNA expression levels in the skin biopsy comprises: (a) isolating RNA from the skin biopsy; (b) using the isolated RNA to create cRNA; (c) labeling the cRNA with a fluorescent dye; and (d) hybridizing the labeled cRNA to a microarray.

A variety of methods are available for obtaining skin biopsies for the methods disclosed herein. In embodiments, a biopsy comprises punch biopsy, shave biopsy, excisional biopsy, and incisional biopsy.

In another embodiment, a method of managing treatment of a subject suffering from atopic dermatitis (AD) is provided, the method comprising: (a) obtaining a pre-treatment skin biopsy from the subject; (b) generating a pre-treatment transcriptional profile comprising RNA expression levels of at least 4 genes selected from the group consisting of SERPINB4, AKR1B10, SERPINB3, S100A7, DEFB4A, RRM2, CCL18, PI3, COL6A6, KRT16, S100A8, RGS1, CCL22, NCAPG, TMPRSS4, KYNU, SELE, GALNT6, PGF, CCL17, APOBEC3A, TYMP, IL27RA, GPR171, GZMB, TACC3, CD1B, CHP2, DIO2, OMD, HSD11B1, GPD1, HPGDS, FAR2, AQP9, PSG7, DKK2, LGR5, ARG1, OGN, CTSV, CARD18, FABP7, MSMB, LOR, SCL46A2, GAL, RNASE7, IL37, PSOR1C2, CRCT1, FADS1, C1orf68, BTC, and LCE2B (i.e., ECZEME55 gene panel); (c) administering to the subject a therapeutic agent; (d) obtaining a post-treatment skin biopsy from the subject; (e) generating a post-treatment transcriptional profile comprising RNA expression levels of the selected genes; (f) comparing the post-treatment transcriptional profile to the pre-treatment transcriptional profile of the selected genes to determine up-regulation and/or down-regulation of expression of the selected genes in response to the therapeutic agent; and (g) administering one or more additional doses of the therapeutic agent to the subject when the comparison of the post-treatment transcriptional profile and the pre-treatment transcriptional profile indicate the RNA expression levels of the selected genes in the subject are up-regulated and/or down-regulated in a manner directionally opposite to RNA expression level changes observed in an AD disease state compared to normal, healthy skin.

In embodiments, the transcriptional profiles comprises data related to the RNA expression levels of genes comprising SERPINB4, AKR1B10, SERPINB3, S100A7, DEFB4A, RRM2, CCL18, PI3, COL6A6 KRT16, S100A8, RGS1, CCL22, NCAPG, TMPRSS4, KYNU, SELE, GALNT6, PGF, CCL17, APOBEC3A, TYMP, IL27RA, GPR171, GZMB, TACC3, CD1B, CHP2, DIO2, OMD, HSD11B1, GPD1, HPGDS, FAR2, AQP9, PSG7, DKK2, LGR5, ARG1, OGN, CTSV, CARD18, FABP7, MSMB, LOR, SCL46A2, GAL, RNASE7, IL37, PSOR1C2, CRCT1, FADS1, C1orf68, BTC, and LCE2B, i.e., (ECZEMA55 gene panel).

In certain embodiments, the transcriptional profiles comprise data related to all 55 genes in the ECZEMA55 set of genes set forth in FIG. 6. In other embodiments, the transcriptional profile may comprise data related to RNA expression levels of a subset of genes selected from ECZEMA55. For example, in some embodiments, the transcriptional profile may comprise at least 4, at least 5, at least 10, at least 15, at least 20, at least 25, at least 30, at least 35, at least 40, at least 45, at least 50, at least 51, at least 52, at least 53, or at least 54 genes selected from the ECZEMA55 gene panel.

In some embodiments, therapeutic agent is an agent effective for the treatment of AD. In a specific embodiment, the therapeutic agent is selected from the group consisting of corticosteroids, betamethasone, tacrolimus, pimecrolimus, narrow-band UVB, PDE4 inhibitors, tofacitinib, dupilumab, and nemolizumab. In a very specific embodiment, the therapeutic agent is betamethasone, pimecrolimus, or dupilumab.

In embodiments, generating a pre-treatment transcriptional profile comprises determining RNA expression levels in the skin biopsy for the selected genes.

In embodiments, determining RNA expression levels comprises molecular methods selected from the group consisting of quantitative RT-PCR, microarray, and RNA-seq. Such methods are known in the art and within the purview of skilled practitioners in the field.

In embodiments, generating a post-treatment transcriptional profile comprises: (a) determining RNA expression levels in the skin biopsy for the selected genes; and (b) comparing the RNA expression levels of the selected genes in the skin biopsy post-treatment to a pre-treatment transcriptional profile to determine the direction of change of RNA expression levels.

In one embodiment, the therapeutic agent is betamethasone and the genes comprise SERPINB4, LOR, CD18, CRCT1, CCL17, BTC, GAL, and FAB7.

In another embodiment, the therapeutic agent is pimecrolimus and the genes comprise FAR2, LCE2B, RNASE7, and CCL18.

In another embodiment, the therapeutic agent is dupilumab and the genes comprise RNASE7, LOR, APOBEC3A, BTC, and AQP9.

In a specific embodiment, the genes are selected from the group consisting of APOBEC3A, AQP9, BTC, CCL17, CCL18, CRCT1, FABP7, FADS1, FAR2, GAL, LCE2B, LOR, RNASE7, and SERPINB4.

EXAMPLES

The following detailed methodology and materials are set forth to support and illustrate particular aspects and embodiments of the invention, and should not be construed as limiting the scope thereof.

Example 1. Identification of AD Signature Genes (89ADGES)

A. Identification of Eligible Gene Expression Datasets and Filtering Criteria

FIG. 1 is a flow chart depicting the major steps of data acquisition and analysis. To identify suitable microarray datasets, NCBI GEO (Gene Expression Omnibus, NCBI) database was studied. Relevant literature that examined DEG genes in AD and non-AD subjects published between 2000 and February 2014 were selected using the search criteria human [organism] AND Atopic Dermatitis AND 2000/01/01:2018/02/28 [Publication Date]. Eligible datasets for study were selected based on the following inclusion criteria: a) the dataset must compare AD patients to healthy (non-AD) controls, and b) the dataset must be generated from same tissue type (i.e. skin). The following information was extracted from each study: (1) GEO accession, (2) sample type, (3) platform, (4) numbers of AD and non-AD individuals, and (5) gene expression values. Visual BASIC macros were used to extract the expression values of individual genes in AD and control samples. All data were derived using Affymetrix platform for human AD and control biopsy tissue samples.

TABLE 1

Multi-origin cutaneous gene expression data sets in NCBI's publicly accessible Gene Expression Omnibus (GEO) database.

| | Cutaneous gene expression data sets in GEO database | Number of biopsy samples eligible for this analysis |
|---|---|---|
| 1 | GSE36842 | 39 |
| 2 | GSE32924 | 33 |
| 3 | GSE16161 | 18 |
| 4 | GSE5667 | 17 |
| 5 | GSE6012 | 20 |

B. Data Analysis

All available AD microarray human datasets that fulfilled the inclusion criteria were downloaded from the NCBI GEO database. Five independent gene expression microarray studies, comprising a total of 127 samples and more than 250,000 transcripts representing approximately 25,000 unique genes (based on Unigene clusters) were utilized. Data tables were constructed containing gene expression values, with genes/probes in rows and samples/experiments in columns using GEO2R, an interactive web tool that processes data tables using the GEOquery, and Limma R packages from the Bioconductor project. GEOquery R package is used to parse GEO data into R data structures that can be used by other R packages. It handles a wide range of experimental designs and data types and applies multiple-testing corrections on p-values to help correct for the occurrence of false positives. Limma provides several p-value adjustment options. These adjustments, also called multiple-testing corrections, attempt to correct for the occurrence of false positive results. The Benjamini and Hochberg false discovery rate was selected as it is the most commonly used adjustment for microarray data and provides a good balance between discovery of statistically significant genes and limitations of false positives. P-values are calculated after adjustment for multiple testing correction. Genes with the smallest p-values ($p<0.05$) are considered most reliable. DEGs present in at least 3 out of 5 datasets (common dataset ratio$\geq 0.6$) were identified and their expression values ranked according to their average fold changes. Unsupervised hierarchical cluster analysis was performed with data obtained from AD and non-AD groups using the program Genesis to detect outliers. Multiple comparison adjustment was applied to derive the adjusted P value using the false discovery rate (FDR). Ingenuity Support Vector Machine and discriminant analysis were used to discriminate and predict membership of AD patients from healthy controls.

C. Selection of Discriminatory Genes

1. Gene Signatures Based on Rank Analysis

In order to gain further insight into the pathogenesis of AD, the genes were ranked according to their p-values and fold changes. For this, the expression values of each DEG was extracted from individual datasets and compared between AD and non-AD controls using the ANOVA module of the GENESIS software suit. Finally, average fold-changes of DEGs were plotted against p-values. The prediction analysis method was used to derive a minimal set of genes that could best discriminate AD from controls.

2. Classification and Prediction of AD Patients Using Discriminant and Support Vector Machine Signature genes were identified among the top 10% ranked genes overlapping among the five GEO datasets. Investigators then ascertained whether these molecular profiling signature genes can be used to discriminate between AD patients and controls. The top 89 genes from five datasets were merged after data normalization and adjusting batch effect using COMBAT. The 89-gene signature (AD Gene Expression Signature, 89ADGES) was used to predict independent AD gene expression data. After combining the five datasets, 10% of the subjects were randomly chosen for testing, and the rest for training. Support vector machine (SVM) was used to analyze data. SVM represents a powerful technique for general (nonlinear) classification, regression and outlier detection and has been widely used in many bioinformatics applications. The SVM function in R package e1071 was used to build the statistical prediction model with C-classification and radial kernel, where the parameters were tuned to give the best prediction results. Using the training data, a final model was obtained with 10-fold validation. Then the final model was used to predict AD for the testing data.

TABLE 2

Classification Matrix for AD Samples Based on 89ADGES and Using Discriminant Analysis Average Accuracy, 98%, n = number of individuals per study group

| GEO ID | Number of | | Classified Sample Group as | | |
|---|---|---|---|---|---|
| | Cases | Controls | Cases | Controls | % Correct |
| GSE36842 | 8 | 15 | 7 | 16 | 98 |
| GSE32924 | 25 | 8 | 25 | 8 | 98 |
| GSE16161 | 9 | 9 | 9 | 9 | 100 |
| GSE5667 | 12 | 5 | 12 | 5 | 100 |
| GSE6012 | 10 | 10 | 10 | 10 | 100 |
| Total | 64 | 47 | 63 | 48 | 98 |

3. Identification of 89ADGES

Table 3 shows the 89ADGES member genes, their log average fold-change values and lowed p-value among the five data sets.

TABLE 3

89ADGES: Common Genes Differentially Regulated in AD Skin Compared to Healthy Skin

| Gene Name | log Avg. FC | Lowest p-value |
|---|---|---|
| Table 3A: 89ADGES members up-regulated in AD | | |
| SERPINB4 | 6.277019432 | $4.27 \times 10^{-09}$ |
| AKR1B10 | 5.544774784 | $5.4 \times 10^{-10}$ |
| SERPINB3 | 4.646773884 | $4.48 \times 10^{-11}$ |
| S100A7 | 4.367522369 | $5.28 \times 10^{-11}$ |
| DEFB4A | 4.246248748 | 0.000000283 |
| RRM2 | 4.096689214 | 0.00000124 |
| CCL18 | 4.005266306 | $2.74 \times 10^{-09}$ |
| PI3 | 4.003801065 | $7.62 \times 10^{-08}$ |
| COL6A6 | 3.902604864 | 0.00000717 |
| KRT16 | 3.847253956 | $3.87 \times 10^{-11}$ |
| S100A8 | 3.444272634 | 0.0000487 |
| RGS1 | 3.4171696 | $2.03 \times 10^{-08}$ |
| CCL22 | 3.350973833 | 0.00000104 |
| NCAPG | 2.955770125 | $1.91 \times 10^{-10}$ |
| TMPRSS4 | 2.931612832 | 0.000142 |

TABLE 3-continued

89ADGES: Common Genes Differentially Regulated in AD Skin Compared to Healthy Skin

| Gene Name | log Avg. FC | Lowest p-value |
|---|---|---|
| KYNU | 2.917508821 | 0.000000459 |
| KRT6 | 2.767921956 | $2.61 \times 10^{-10}$ |
| SELE | 2.446403227 | 0.000579 |
| GALNT6 | 2.367450784 | $4.78 \times 10^{-08}$ |
| PGF | 2.326221816 | $2.39 \times 10^{-09}$ |
| CCL17 | 2.277567843 | 0.00129 |
| APOBEC3A | 2.247232971 | 0.000209 |
| TYMP | 2.09796741 | 0.0000058 |
| IL27RA | 2.043993933 | 0.0000027 |
| GPR171 | 2.018769024 | 0.00134 |
| GZMB | 1.982573983 | 0.000534 |
| EHBP1L1 | 1.906204353 | 0.00000385 |
| TACC3 | 1.902825307 | 0.000000096 |
| CBLC | 1.838749796 | 0.0000767 |
| CD1B | 1.709019751 | 0.00128 |
| IGL | 0.676398326 | 0.00825 |
| Table 3B: 89ADGES members down-regulated in AD | | |
| LCE2B | -3.597617986 | 0.000000373 |
| CDSN | -3.394592086 | 0.00000142 |
| BTC | -3.219759779 | $4.6 \times 10^{-11}$ |
| C1orf46 | -3.182991348 | $1.01 \times 10^{-09}$ |
| C1orf68 | -3.138513214 | $4.86 \times 10^{-09}$ |
| FADS1 | -3.1154601 | 0.00114 |
| CRCT1 | -3.069033076 | 0.000000123 |
| ASPRV1 | -2.914325671 | 0.00000012 |
| PSORS1C2 | -2.861260593 | $4.13 \times 10^{-14}$ |
| SERPINB7 | -2.823255842 | 0.000000146 |
| IL1F7 | -2.739229063 | $4.83 \times 10^{-11}$ |
| RNASE7 | -2.649385595 | $7.23 \times 10^{-13}$ |
| GAL | -2.637722476 | 0.00122 |
| SLC46A2 | -2.545903366 | 0.00000029 |
| POF1B | -2.495361201 | $3.06 \times 10^{-08}$ |
| LOR | -2.494151427 | 0.00000391 |
| SLURP1 | -2.475406805 | 0.0000368 |
| MSMB | -2.451843983 | $7.91 \times 10^{-11}$ |
| CST6 | -2.43422782 | 0.00000529 |
| HBB | -2.434136836 | 0.00000163 |
| ELMOD1 | -2.433199491 | $8.63 \times 10^{-08}$ |
| CORIN | -2.375731053 | 0.00000403 |
| FABP7 | -2.346465663 | 0.00000719 |
| SCGB2A1 | -2.332382368 | 0.000477 |
| CARD18 | -2.306800065 | 0.00000871 |
| CTSL2 | -2.292130989 | 0.000000116 |
| OGN | -2.290838046 | 0.000000173 |
| LOC100130476 | -2.28997722 | 0.0000955 |
| GREM1 | -2.264842093 | 0.0000119 |
| GPLD1 | -2.250590912 | 0.00000399 |
| HBA | -2.195108511 | 0.00000891 |
| ARG1 | -2.190658534 | 0.0000995 |
| ANXA9 | -2.171055714 | $2.65 \times 10^{-08}$ |
| LGR5 | -2.164211436 | 0.000062 |
| DKK2 | -2.160127506 | $3.12 \times 10^{-08}$ |
| KLK5 | -2.146388522 | 0.00017 |
| LYVE1 | -2.14637781 | 0.000000121 |
| PSG7 | -2.123047267 | 0.0000028 |
| C15orf48 | -2.109870314 | 0.00000193 |
| AQP9 | -2.067261314 | $6.68 \times 10^{-13}$ |
| FAR2 | -1.998330051 | 0.0035 |
| HPGDS | -1.980138147 | $2.89 \times 10^{-08}$ |
| CPA3 | -1.959796917 | 0.0000139 |
| GPD1 | -1.940045793 | 0.000533 |
| SLIT2 | -1.935228706 | 0.000000344 |
| HSD11B1 | -1.920308409 | 0.000000167 |
| IGJ | -1.916732525 | 0.000486 |
| ARHGAP18 | -1.905788915 | $9.69 \times 10^{-16}$ |
| EREG | -1.905652034 | 0.0000189 |
| CLDN23 | -1.856469032 | $2.18 \times 10^{-08}$ |
| SFRP2 | -1.832980742 | 0.0114 |
| FLG | -1.832369022 | 0.000011 |
| MUC15 | -1.828317258 | 0.0000388 |
| SCEL | -1.804613552 | $7.49 \times 10^{-09}$ |
| OMD | -1.801206413 | 0.000000029 |

TABLE 3-continued

89ADGES: Common Genes Differentially Regulated in AD Skin Compared to Healthy Skin

| Gene Name | log Avg. FC | Lowest p-value |
| --- | --- | --- |
| LOX | −1.798074936 | 0.000000746 |
| DIO2 | −1.703367409 | 0.0000115 |
| CHP2 | −1.489311424 | 0.0000376 |

4. Validation of 89ADGES Subset in Mouse Model of AD

Expression profiles of genes were evaluated using quantitative real-time polymerase chain reaction (qRT-PCR) in a mouse model that shows all hallmarks of AD. Briefly, BALB/c mice (Harlan Laboratories, Indianapolis, Ind.) maintained in a specific pathogen-free environment were used for this study following ethical guidelines of the Institutional Animal Care and Use Committee approved by the Veterinary Service Department of the Cincinnati Children's Hospital Medical Center Research foundation. AD was induced as previously described. Fluhr J W, et al. *Stratum corneum acidification in neonatal skin: secretory phospholipase A2 and the sodium/hydrogen antiporter-1 acidify neonatal rat stratum corneum, J Invest Dermatol* 122: 320-9 (2004); Zhang Z, et al., *EGFR signaling blunts allergen-induced IL-6 production and Th17 responses in the skin and attenuates development and relapse of atopic dermatitis, J Immunol* 192: 859-66 (2014). Mice (AD and control; seven per group) were anesthetized, backs shaved 1 day before the first allergen exposure, and either 200 µl of saline water or *Aspergillus fumigatus* extract (Greer Laboratories, Lenoir, N.C.; 1 mg/ml re-suspended in saline) was applied using a 2×2-cm patch of sterile gauze. Quantitative PCR analysis was performed using primer sequences of genes as shown in Table 4.

TABLE 4 qPCR Primer Sequences

| | | |
| --- | --- | --- |
| HPRT | Forward | 5'-TGCCGAGGATTTGGAAAAAG-3'<br>SEQ ID NO: 1 |
| | Reverse | 5'-CCCCCCTTGAGCACACAG-3'<br>SEQ ID NO: 2 |
| S100A8 | Forward | 5'-CCATGCCCTCTAGAAGAATG-3'<br>SEQ ID NO: 3 |
| | Reverse | 5'-ATCACCATCGCAAGGAACTC-3'<br>SEQ ID NO: 4 |
| Serpinb3a | Forward | 5'-CAGATGATGAAACAAAACATCG-3'<br>SEQ ID NO: 5 |
| | Reverse | 5'-AGACCTTGAGTGCTGCTCATA-3'<br>SEQ ID NO: 6 |
| KRT6B | Forward | 5'-AACCTGCAAGCTGCTAT-3'<br>SEQ ID NO: 7 |
| | Reverse | 5'-CTTGACATTCATGAGTTCCTGGTA-3'<br>SEQ ID NO: 8 |
| CLDN23 | Forward | 5'-AGAAAAGAAGACAGCCACCTC-3'<br>SEQ ID NO: 9 |
| | Reverse | 5'-CAGAAGTTCAAGTCACCCTCAG-3'<br>SEQ ID NO: 10 |
| DEFB4 | Forward | 5'-GATCCATTACCTTCTCTTCACATTTC-3'<br>SEQ ID NO: 11 |
| | Reverse | 5'-CTCCATTGGTCATGCATGTTATT-3'<br>SEQ ID NO: 12 |
| CCL22 | Forward | 5'-CTTCTTGCTGTGGCAATTC-3'<br>SEQ ID NO: 13 |
| | Reverse | 5'-TGATGGGAGAGGGTGAC-3'<br>SEQ ID NO: 14 |
| LOR | Forward | 5'-ACATCAGCATCACCTCCTTC-3'<br>SEQ ID NO: 15 |
| | Reverse | 5'-TCTTTCCACAACCCAGAGG-3'<br>SEQ ID NO: 16 |
| CST6 | Forward | 5'-AGCGACAGCCTCTACTACTT-3'<br>SEQ ID NO: 17 |
| | Reverse | 5'-CGGCACTCTGTGCTTTCTAT-3'<br>SEQ ID NO: 18 |

Figure 2:
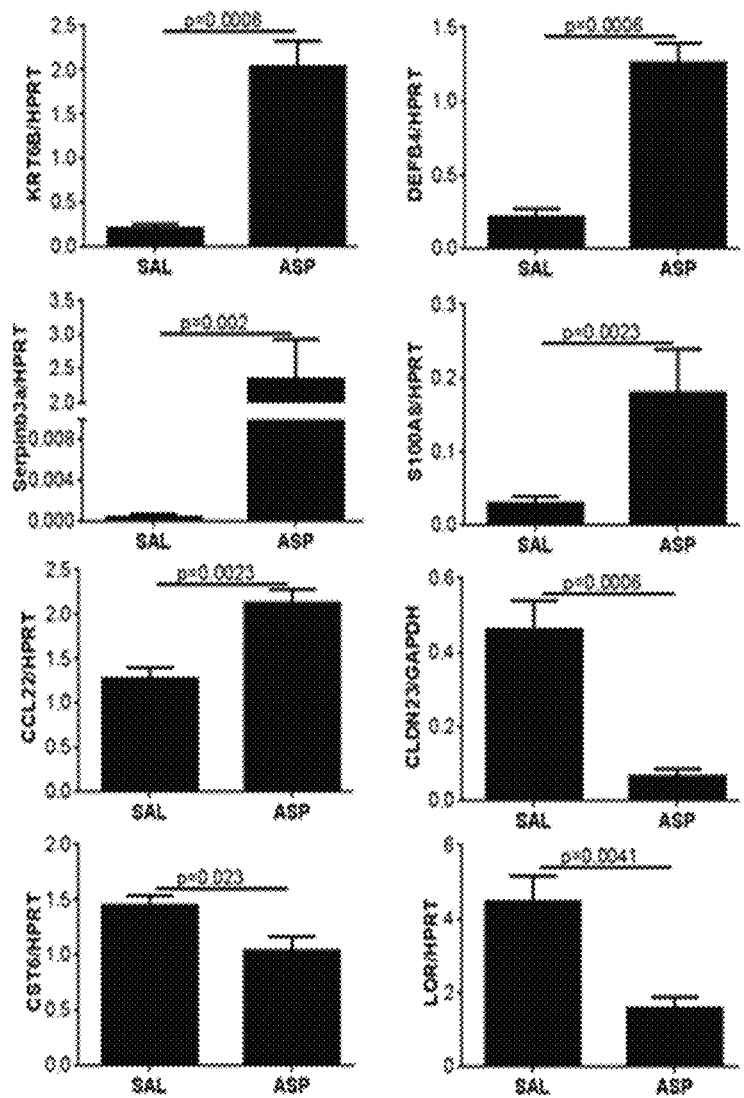
FIG. 2 shows qPCR validation of representative up-regulated (KRT6B, SERPINB, CCL22, DEFB4, and S100A8) and down-regulated (CST6, CLDN23, and LOR) genes in a mouse model of AD. HPRT was used as a housekeeping gene.

Results are shown in FIG. 2. Statistical significance between the groups (seven for each) was calculated by the Mann Whitney Test and p-values have been indicated. ASP stands for *Aspergillus*-treated AD group, while SAL denotes saline-treated control group. This experiment has been performed as a technological confirmation to check the direction of the expression change of the genes S100A8, Serpinb3a, KRT6B, CLDN23, DEFB4, CCL22, LOR and CST6, which corroborated with the database analysis results. HPRT was used as a housekeeping gene. KRT6B, SERPINB, CCL22, DEFB4 and S100A8 were up-regulated in allergen-treated AD mouse group, while CST6, CLDN23 and LOR were downregulated compared to saline-treated control mice.

Example 2. Development of a Customizable Gene Panel for Assessing AD Treatment Outcomes A. Treatment-Associated Cutaneous Gene Expression Datasets Pre- and post-treatment gene expression datasets have been retrieved from publicly accessible database NCBI GEO, including datasets related to three widely-used treatments for AD: betamethasone and pimecrolimus (NCBI GEO data GSE32473), and dupilumab 300 mg (NCBI GEO data GSE59294).

B. Treatment-Associated DEGs Overlapping with 89ADGES

Analysis of pre-vs. post-treatment gene expression data shows that there are substantial overlaps between 89ADGES and the genes that are significantly differentially regulated in the three analyzed treatment options. Table 5 shows overlap between 89ADGES and betamethasone-related DEGs. Members of 89ADGES that are differentially regulated due to the application of betamethasone to AD skin lesions. Table shows 45 genes that are differentially regulated in treated biopsy samples compared to baseline pre-treatment condition (Fold Change ≥2.0, p-value<0.05) and their corresponding Affymetrix array Identifiers. CCL18, MSMB, SERPINB3 and SERPINB4 genes are associated with multiple array IDs.

TABLE 5

Overlap between 89ADGES and Betamethasone-Related DEGs

| | Gene Symbol | Affymetrix ID |
|---|---|---|
| 1 | AKR1B10 | 206561_s_at |
| 2 | APOBEC3A | 210873_x_at |
| 3 | AQP9 | 205568_at |
| 4 | ARG1 | 206177_s_at |
| 5 | C15orf48 | 223484_at |
| 6 | C1orf68 | 217087_at |
| 7 | CARD18 | 231733_at |
| 8 | CCL17 | 207900_at |
| 9 | CCL18 | 209924_at, 32128_at |
| 10 | CCL22 | 207861_at |
| 11 | CD1B | 206749_at |
| 12 | COL6A6 | 230867_at |
| 13 | CRCT1 | 220620_at |
| 14 | CTSV | 210074_at |
| 15 | DIO2 | 231240_at |
| 16 | DKK2 | 219908_at |
| 17 | FABP7 | 205030_at |
| 18 | FADS1 | 208963_x_at |
| 19 | FAR2 | 220615_s_at |
| 20 | GAL | 214240_at |
| 21 | GPR171 | 207651_at |
| 22 | GZMB | 210164_at |
| 23 | HPGDS | 206726_at |
| 24 | HSD11B1 | 205404_at |
| 25 | IGLJ3 | 214677_x_at |
| 26 | IL37 | 221470_s_at |
| 27 | KRT16 | 209800_at |
| 28 | KYNU | 217388_s_at |
| 29 | LGR5 | 213880_at |
| 30 | MSMB | 207430_s_at, 210297_s_at |
| 31 | NCAPG | 218663_at |
| 32 | OMD | 205907_s_at |
| 33 | PGF | 209652_s_at |
| 34 | PI3 | 41469_at |
| 35 | PSG7 | 205602_x_at |
| 36 | PSORS1C2 | 220635_at |
| 37 | RGS1 | 216834_at |
| 38 | RRM2 | 209773_s_at |
| 39 | S100A8 | 214370_at |
| 40 | SELE | 206211_at |
| 41 | SERPINB3 | 209719_x_at, 209720_s_at |
| 42 | SERPINB4 | 210413_x_at, 211906_s_at |
| 43 | SLC46A2 | 223816_at |
| 44 | TACC3 | 218308_at |
| 45 | TMPRSS4 | 218960_at |

Table 6 shows members of 89ADGES that are differentially regulated due to the application of pimecrolimus on to AD skin lesions. Table shows 41 genes that are differentially regulated in treated biopsy samples compared to baseline pre-treatment condition (Fold Change ≥2.0, p-value<0.05) and their corresponding Affymetrix array Identifiers. BTC, CCL18, MSMB, IL-37, SERPINB3 and SERPINB4 genes are associated with multiple array IDs.

TABLE 6

Overlap between 89ADGES and Pimecrolimus-Related DEGs

| | Gene Symbol | Affymetrix ID |
|---|---|---|
| 1 | AKR1B10 | 206561_s_at |
| 2 | APOBEC3A | 210873_x_at |
| 3 | AQP9 | 205568_at |
| 4 | BTC | 207326_at, 241412_at |
| 5 | C1orf68 | 217087_at |
| 6 | CCL18 | 209924_at, 32128_at |
| 7 | CCL22 | 207861_at |
| 8 | CD1B | 206749_at |
| 9 | CHP2 | 206149_at |
| 10 | COL6A6 | 230867_at |
| 11 | CTSV | 210074_at |
| 12 | DEFB4A/DEFB4B | 207356_at |
| 13 | FABP7 | 205030_at |
| 14 | GAL | 214240_at |
| 15 | GALNT6 | 219956_at |
| 16 | GPD1 | 213706_at |
| 17 | GZMB | 210164_at |
| 18 | HSD11B1 | 205404_at |
| 19 | IL27RA | 222062_at |
| 20 | IL37 | 221470_s_at, 224555_x_at |
| 21 | KRT16 | 209800_at |
| 22 | KYNU | 217388_s_at |
| 23 | LCE2B | 207710_at |
| 24 | LINC00302 | 216935_at |
| 25 | LOC100130476 | 243871_at |
| 26 | LOR | 207720_at |
| 27 | MSMB | 207430_s_at, 210297_s_at |
| 28 | PGF | 209652_s_at |
| 29 | PI3 | 41469_at |
| 30 | PSORS1C2 | 220635_at |
| 31 | RGS1 | 216834_at |
| 32 | RNASE7 | 233488_at |
| 33 | RRM2 | 209773_s_at |
| 34 | S100A7 | 205916_at |
| 35 | S100A8 | 214370_at |
| 36 | SELE | 206211_at |
| 37 | SERPINB3 | 209719_x_at, 209720_s_at |
| 38 | SERPINB4 | 210413_x_at, 211906_s_at |
| 39 | SLC46A2 | 223816_at |
| 40 | TMPRSS4 | 218960_at |
| 41 | TYMP | 217497_at |

Table 7 shows members of 89ADGES that are differentially regulated due to the administration of dupilumab. Table shows 42 genes that are differentially regulated in treated biopsy samples compared to baseline pre-treatment condition (Fold Change ≥2.0, p-value<0.05) and their corresponding Affymetrix array Identifiers. CCL18, IL-37, SERPINB3 and SERPINB4 genes are associated with multiple array IDs.

TABLE 7

Overlap between 89ADGES and Dupilumab-Related DEGs

| | Gene Symbol | Affymetrix ID |
|---|---|---|
| 1 | AKR1B10 | 206561_s_at |
| 2 | APOBEC3A | 210873_x_at |
| 3 | BTC | 241412_at |
| 4 | C15orf48 | 223484_at |
| 5 | CCL17 | 207900_at |
| 6 | CCL18 | 209924_at, 32128_at |
| 7 | CCL22 | 207861_at |
| 8 | CD1B | 206749_at |
| 9 | CHP2 | 206149_at |
| 10 | COL6A6 | 230867_at |
| 11 | DEFB4A/DEFB4B | 207356_at |
| 12 | DIO2 | 231240_at |
| 13 | DKK2 | 219908_at |
| 14 | GALNT6 | 219956_at |
| 15 | GPD1 | 213706_at |
| 16 | GPR171 | 207651_at |
| 17 | GZMB | 210164_at |
| 18 | HBB | 209116_x_at |
| 19 | HPGDS | 206726_at |
| 20 | IGLJ3 | 214677_x_at |
| 21 | IL27RA | 222062_at |
| 22 | IL37 | 221470_s_at, 224555_x_at |
| 23 | JCHAIN | 212592_at |

TABLE 7-continued

Overlap between 89ADGES and Dupilumab-Related DEGs

| | Gene Symbol | Affymetrix ID |
|---|---|---|
| 24 | KRT16 | 209800_at |
| 25 | KYNU | 217388_s_at |
| 26 | LGR5 | 213880_at |
| 27 | LOC100130476 | 243871_at |
| 28 | MSMB | 210297_s_at |
| 29 | NCAPG | 218663_at |
| 30 | OGN | 222722_at |
| 31 | OMD | 205907_s_at |
| 32 | PGF | 209652_s_at |
| 33 | PI3 | 41469_at |
| 34 | RGS1 | 216834_at |
| 35 | RRM2 | 209773_s_at |
| 36 | S100A8 | 214370_at |
| 37 | SELE | 206211_at |
| 38 | SERPINB3 | 209719_x_at, 209720_s_at |
| 39 | SERPINB4 | 210413_x_at, 211906_s_at |
| 40 | SLC46A2 | 223816_at |
| 41 | TMPRSS4 | 218960_at |
| 42 | TYMP | 217497_at |

C. Identification of the Panel Genes for Assessing Treatment Options

The gene panel has been developed by combining three datasets and removing duplicate entries to include all unique treatment-responsive gene entries. This will ensure that the gene panel ("ECZEMA55") will include all AD-relevant 89ADGES member genes that are differentially regulated in three different treatment options. Table 8 shows the symbols, number of treatment datasets where the gene is differentially regulated. Entrez Gene Names, cellular location and functional type of ECZEMA55 panel genes. ECZEMA55 represents a panel of fifty-five genes that includes AD-relevant 89ADGES member genes that are differentially regulated in all three different treatments.

TABLE 8

ECZEMA55 Gene Panel Members

| Symbol | Datasets | Entrez Gene Name | Location | Type(s) |
|---|---|---|---|---|
| AKR1B10 | 3 | aldo-keto reductase family 1 member B10 | Cytoplasm | enzyme |
| APOBEC3A | 3 | apolipoprotein B mRNA editing enzyme catalytic subunit 3A | Cytoplasm | enzyme |
| AQP9 | 2 | aquaporin 9 | Plasma Membrane | transporter |
| ARG1 | 1 | arginase 1 | Cytoplasm | enzyme |
| BTC | 2 | betacellulin | Extracellular Space | growth factor |
| CARD18 | 2 | caspase recruitment domain family member 18 | Cytoplasm | other |
| CCL17 | 2 | C-C motif chemokine ligand 17 | Extracellular Space | cytokine |
| CCL18 | 1 | C-C motif chemokine ligand 18 | Extracellular Space | cytokine |
| CCL22 | 2 | C-C motif chemokine ligand 22 | Extracellular Space | cytokine |
| CD1B | 2 | CD1b molecule | Plasma Membrane | other |
| CHP2 | 2 | calcineurin like EF-hand protein 2 | Cytoplasm | other |
| COL6A6 | 3 | collagen type VI alpha 6 chain | Extracellular Space | other |
| CRCT1 | 2 | cysteine rich C-terminal 1 | Other | other |
| CTSV | 3 | cathepsin V | Cytoplasm | peptidase |
| DEFB4A | 1 | defensin beta 4A | Extracellular Space | other |
| DEFB4B | 2 | defensin beta 4B | Extracellular Space | other |
| DIO2 | 2 | iodothyronine deiodinase 2 | Cytoplasm | enzyme |
| DKK2 | 2 | dickkopf WNT signaling pathway inhibitor 2 | Extracellular Space | other |
| FABP7 | 2 | fatty acid binding protein 7 | Cytoplasm | transporter |
| FADS1 | 2 | fatty acid desaturase 1 | Plasma Membrane | enzyme |
| FAR2 | 1 | fatty acyl-CoA reductase 2 | Cytoplasm | enzyme |
| GAL | 1 | galanin and GMAP prepropeptide | Extracellular Space | other |
| GALNT6 | 2 | polypeptide N-acetylgalactosaminyltransferase 6 | Cytoplasm | enzyme |
| GPD1 | 2 | glycerol-3-phosphate dehydrogenase 1 | Cytoplasm | enzyme |
| GPR171 | 2 | G protein-coupled receptor 171 | Plasma Membrane | G-protein coupled receptor |
| GZMB | 1 | granzyme B | Cytoplasm | peptidase |
| HPGDS | 3 | hematopoietic prostaglandin D synthase | Cytoplasm | enzyme |
| HSD11B1 | 1 | hydroxysteroid 11-beta dehydrogenase 1 | Cytoplasm | enzyme |
| IL27RA | 2 | interleukin 27 receptor subunit alpha | Plasma Membrane | transmembrane receptor |

TABLE 8-continued

ECZEMA55 Gene Panel Members

| Symbol | Data-sets | Entrez Gene Name | Location | Type(s) |
|---|---|---|---|---|
| IL37 | 2 | interleukin 37 | Extracellular Space | cytokine |
| KRT16 | 2 | keratin 16 | Cytoplasm | other |
| KYNU | 2 | kynureninase | Cytoplasm | enzyme |
| LCE2B | 3 | late cornified envelope 2B | Other | other |
| LGR5 | 1 | leucine rich repeat containing G protein-coupled receptor 5 | Plasma Membrane | transmembrane receptor |
| LOR | 3 | loricrin | Cytoplasm | other |
| MSMB | 3 | microseminoprotein beta | Extracellular Space | other |
| NCAPG | 1 | non-SMC condensin I complex subunit G | Nucleus | other |
| OGN | 2 | osteoglycin | Extracellular Space | growth factor |
| OMD | 1 | osteomodulin | Extracellular Space | other |
| PGF | 2 | placental growth factor | Extracellular Space | growth factor |
| PI3 | 1 | peptidase inhibitor 3 | Extracellular Space | other |
| PSG7 | 3 | pregnancy specific beta-1-glycoprotein 7 (gene/pseudogene) | Extracellular Space | other |
| PSORS1C2 | 2 | psoriasis susceptibility 1 candidate 2 | Extracellular Space | other |
| RGS1 | 1 | regulator of G protein signaling 1 | Plasma Membrane | other |
| RNASE7 | 2 | ribonuclease A family member 7 | Extracellular Space | enzyme |
| RRM2 | 3 | ribonucleotide reductase regulatory subunit M2 | Nucleus | enzyme |
| S100A7 | 2 | S100 calcium binding protein A7 | Cytoplasm | other |
| S100A8 | 1 | S100 calcium binding protein A8 | Cytoplasm | other |
| SELE | 2 | selectin E | Plasma Membrane | transmembrane receptor |
| SERPINB3 | 2 | serpin family B member 3 | Cytoplasm | other |
| SERPINB4 | 1 | serpin family B member 4 | Cytoplasm | other |
| SLC46A2 | 3 | solute carrier family 46 member 2 | Plasma Membrane | transporter |
| TACC3 | 1 | transforming acidic coiled-coil containing protein 3 | Nucleus | other |
| TMPRSS4 | 3 | transmembrane serine protease 4 | Other | peptidase |
| TYMP | 3 | thymidine phosphorylase | Extracellular Space | growth factor |

Example 3. Describing Treatment Responses Using AD-Relevant Treatment-Responsive Genes Gene expression data related to ECZEMA55 genes were extracted for pre- and post-treatment samples. Values were expressed as post-treatment/pre-treatment ratio. Variable selection or feature selection was performed by clustering of 55 genes into smaller number of coherent clusters and identifying the most representative gene per cluster. Representative genes were used to build a regression model which can be used to efficiently model the data. Outcome variable was defined either as the reduction in symptom score (available as per subject pEASI reduction; pEASI=partial EASI reduction in dataset GSE32473) or as the post-treatment symptom score (taking pre-treatment symptom score as an independent covariate and per subject pre-treatment symptom scores is available, as in the dataset GSE59294). A regression model was generated and regression trees were constructed. Classification/prediction and efficiency of the model were determined.

A. Betamethasone Drug Effect

Gene expression matrix from GSE32473 dataset was used to model the effect. Variable Clustering was used for assessing collinearity in 55-treatment gene expression and to resolve the data into clusters that can be scored as a single variable. This provides a way for grouping similarly behaving genes (variables) into representative groups. Each cluster can be represented by a single component transcript (independent variable), which is a linear combination of all transcript variables in the cluster.

The fold-change (post-treatment/pre-treatment) of expression values of the ECZEMA55 member genes have been clustered using JMP® SAS® program. Paired punch biopsy samples collected before and after treatment have been used to identify post-vs. pre-treatment responses of betamethasone. The result shows that the responses of the ECZEMA55 member genes to betamethasone treatment can be grouped into 11 correlated clustered, with each cluster predominantly represented by the post-vs. pre-treatment response of one predominant gene in the cluster (Table 9). Top clusters that include most of the variables were taken for down-stream regression analysis. Table 9 shows the number of ECZEMA55 treatments-responsive genes (variables) in each cluster, most representative gene variable in the cluster along with Cluster Proportion of Variation Explained and Total Proportion of Variation Explained. Betamethasone response can be grouped into 11 clusters. They are arranged by the number of member genes they contain.

TABLE 9

ECZEMA55 Betamethasone Treatment Responsive Genes

| Cluster | Number of Members | Most Representative Variable | Cluster Proportion of Variation Explained | Total Proportion of Variation Explained |
|---|---|---|---|---|
| 1 | 19 | SERPINB4 | 0.856 | 0.267 |
| 3 | 8 | LOR | 0.811 | 0.106 |
| 4 | 7 | CRCT1 | 0.699 | 0.08 |
| 5 | 4 | CCL17 | 0.868 | 0.057 |
| 7 | 5 | BTC_1 | 0.689 | 0.056 |
| 2 | 4 | GAL | 0.859 | 0.056 |
| 6 | 3 | FABP7 | 0.866 | 0.043 |
| 9 | 3 | IL27RA | 0.817 | 0.04 |
| 10 | 3 | TACC3 | 0.784 | 0.039 |
| 11 | 3 | DKK2 | 0.715 | 0.035 |
| 8 | 2 | MSMB_2 | 0.754 | 0.025 |

Table 10 shows the clustered behavior of ECZEMA55 member genes due to betamethasone treatment. Member genes in each cluster have been shown with their RSquare values with own cluster RSquare with nest closest cluster and 1-RSquare ratios.

TABLE 10

ECZEMA55 member gene clustered behavior with betamethasone treatment

| Cluster | Members | RSquare with Own Cluster | RSquare with Next Closest | 1-RSquare Ratio |
|---|---|---|---|---|
| 1 | AKR1B10 | 0.928 | 0.601 | 0.179 |
| 1 | CCL18_1 | 0.974 | 0.663 | 0.078 |
| 1 | CCL18_2 | 0.969 | 0.696 | 0.102 |
| 1 | CCL22 | 0.964 | 0.563 | 0.082 |
| 1 | CD1B | 0.985 | 0.625 | 0.041 |
| 1 | COL6A6 | 0.699 | 0.507 | 0.612 |
| 1 | DEFB4A | 0.978 | 0.616 | 0.058 |
| 1 | DIO2 | 0.521 | 0.332 | 0.717 |
| 1 | GALNT6 | 0.778 | 0.735 | 0.84 |
| 1 | GPR171 | 0.597 | 0.452 | 0.735 |
| 1 | KRT16 | 0.97 | 0.678 | 0.094 |
| 1 | PI3 | 0.902 | 0.544 | 0.215 |
| 1 | RGS1 | 0.858 | 0.678 | 0.44 |
| 1 | RRM2 | 0.764 | 0.405 | 0.397 |
| 1 | S100A7 | 0.524 | 0.385 | 0.773 |
| 1 | SERPINB3_1 | 0.978 | 0.602 | 0.055 |
| 1 | SERPINB3_2 | 0.953 | 0.517 | 0.097 |
| 1 | SERPINB4 | 0.992 | 0.596 | 0.021 |
| 1 | TMPRSS4 | 0.936 | 0.566 | 0.147 |
| 2 | FAR2 | 0.798 | 0.702 | 0.677 |
| 2 | GAL | 0.908 | 0.23 | 0.119 |
| 2 | LGR5 | 0.904 | 0.635 | 0.263 |
| 2 | TYMP | 0.825 | 0.265 | 0.239 |
| 3 | IL1F7_1 | 0.642 | 0.11 | 0.403 |
| 3 | IL1F7_2 | 0.926 | 0.105 | 0.083 |
| 3 | LOR | 0.943 | 0.133 | 0.066 |
| 3 | OGN | 0.745 | 0.292 | 0.361 |
| 3 | OMD | 0.899 | 0.246 | 0.134 |
| 3 | PSORS1C2 | 0.551 | 0.448 | 0.814 |
| 3 | S100A8 | 0.852 | 0.309 | 0.214 |
| 3 | SLC46A2 | 0.929 | 0.154 | 0.084 |
| 4 | ARG1 | 0.719 | 0.289 | 0.395 |
| 4 | CRCT1 | 0.945 | 0.353 | 0.085 |
| 4 | CTSL2 | 0.854 | 0.351 | 0.225 |
| 4 | HSD11B1 | 0.811 | 0.259 | 0.256 |
| 4 | LCE2B | 0.886 | 0.43 | 0.199 |
| 4 | PGF | 0.351 | 0.249 | 0.864 |
| 4 | RNASE7_2 | 0.329 | 0.262 | 0.908 |
| 5 | APOBEC3A | 0.961 | 0.16 | 0.046 |
| 5 | CCL17 | 0.982 | 0.167 | 0.022 |
| 5 | RNASE7_22 | 0.851 | 0.231 | 0.194 |
| 5 | SELE | 0.679 | 0.448 | 0.581 |
| 6 | FABP7 | 0.957 | 0.663 | 0.128 |
| 6 | FADS1 | 0.906 | 0.518 | 0.194 |
| 6 | GPD1 | 0.734 | 0.425 | 0.463 |
| 7 | AQP9 | 0.676 | 0.32 | 0.476 |
| 7 | BTC_1 | 0.805 | 0.253 | 0.261 |
| 7 | CARD18 | 0.529 | 0.227 | 0.609 |
| 7 | PSG7 | 0.716 | 0.182 | 0.347 |
| 7 | RNASE7_1 | 0.718 | 0.494 | 0.557 |
| 8 | CHP2 | 0.754 | 0.303 | 0.353 |
| 8 | MSMB_2 | 0.754 | 0.093 | 0.271 |
| 9 | GZMB | 0.687 | 0.421 | 0.541 |
| 9 | IL27RA | 0.902 | 0.546 | 0.217 |
| 9 | KYNU | 0.864 | 0.555 | 0.305 |
| 10 | MSMB_1 | 0.626 | 0.198 | 0.466 |
| 10 | NCAPG | 0.86 | 0.479 | 0.269 |
| 10 | TACC3 | 0.865 | 0.346 | 0.206 |
| 11 | BTC_2 | 0.333 | 0.137 | 0.773 |
| 11 | DKK2 | 0.967 | 0.61 | 0.084 |
| 11 | HPGDS | 0.844 | 0.617 | 0.406 |

TABLE 11

Regression model using representative genes as the predictor variables and the change in symptom score (post- vs. pre-treatment) as the outcome variable for betamethasone

| | Estimate | Std. Error | t value | Pr(>|t|) |
|---|---|---|---|---|
| (Intercept) | 3.472e+00 | 5.073e+00 | 0.684 | 0.6179 |
| SERPINB4 | -2.352e+03 | 1.174e+02 | -20.034 | 0.0318 * |
| LOR | 3.593e+00 | 2.650e-01 | 13.559 | 0.0469 * |
| CD1B | 7.098e+02 | 3.454e+01 | 20.550 | 0.0310 * |
| CRCT1 | -8.053e+01 | 3.410e+00 | -23.613 | 0.0269 * |
| CCL17 | 8.654e+00 | 9.418e-01 | 9.188 | 0.0690 . |
| BTC_1 | 1.329e+01 | 8.193e-01 | 16.221 | 0.0392 * |
| GAL | 6.400e-01 | 9.048e-02 | 7.074 | 0.0894 . |
| FABP7 | 1.989e+00 | 2.156e-01 | 9.227 | 0.0687 . |

Signif. codes: 0 '*' 0.001 '' 0.01 '*' 0.05 '.' 0.1 ' ' 1
(Dispersion parameter for gaussian family taken to be 11.24768)
Null deviance: 11324.100 on 9 degrees of freedom
Residual deviance: 11.248 on 1 degrees of freedom
AIC: 49.555

Number of Fisher scoring iterations: 2

B. Pimecrolimus Drug Effect

The fold-change (post-treatment/pre-treatment) of expression values of the ECZEMA55 member genes have been clustered using JMP® SAS® program. Paired punch biopsy samples collected before and after treatment have been used to identify post-vs. pre-treatment responses of Pimecrolimus. The result shows that the responses of the ECZEMA55 member genes to Pimecrolimus treatment can grouped into multiple correlated clusters, with each cluster predominantly represented by the post-vs. pre-treatment response of one predominant gene in the cluster. Pimcrolimus-response can be grouped into 13 clusters (Table 12). Top 5 clusters including most variables were taken for down-stream regression analysis connecting the change in gene expression with the change in symptom score.

TABLE 12

ECZEMA55 Pimecrolimus treatment responsive genes

| Cluster | Number of Members | Most Representative Variable | Cluster Proportion of Variation Explained | Total Proportion of Variation Explained |
|---|---|---|---|---|
| 1 | 9 | FAR2 | 0.788 | 0.116 |
| 5 | 7 | LCE2B | 0.797 | 0.091 |
| 8 | 6 | RNASE7 | 0.793 | 0.078 |
| 2 | 6 | KRT16 | 0.77 | 0.076 |
| 4 | 6 | CCL18_1 | 0.692 | 0.068 |
| 3 | 4 | ARG1 | 0.919 | 0.06 |
| 6 | 5 | SERPINB3_1 | 0.729 | 0.06 |
| 12 | 4 | IL1F7_1 | 0.907 | 0.059 |
| 10 | 5 | RRM2 | 0.709 | 0.058 |
| 13 | 3 | PSG7 | 0.758 | 0.037 |
| 11 | 2 | OMD | 0.892 | 0.029 |
| 7 | 2 | CARD18 | 0.77 | 0.025 |
| 9 | 2 | HSD11B1 | 0.679 | 0.022 |

Proportion of variable explained by clustering = 0.781

TABLE 13

ECZEMA55 member gene clustered behavior with pimecrolimus treatment

| Cluster | Members | RSquare with Own Cluster | RSquare with Next Closest cluster | 1-RSquare Ratio |
|---|---|---|---|---|
| 1 | FABP7 | 0.654 | 0.489 | 0.677 |
| 1 | SELE | 0.904 | 0.552 | 0.214 |
| 1 | HPGDS | 0.746 | 0.334 | 0.381 |
| 1 | DEFB4A | 0.878 | 0.451 | 0.223 |
| 1 | APOBEC3A | 0.924 | 0.533 | 0.162 |
| 1 | GAL | 0.963 | 0.545 | 0.082 |
| 1 | TYMP | 0.658 | 0.328 | 0.509 |
| 1 | DKK2 | 0.387 | 0.313 | 0.893 |
| 1 | FAR2 | 0.978 | 0.561 | 0.051 |
| 2 | AKR1B10 | 0.702 | 0.582 | 0.714 |
| 2 | MSMB_2 | 0.799 | 0.216 | 0.256 |
| 2 | KRT16 | 0.906 | 0.471 | 0.177 |
| 2 | NCAPG | 0.7 | 0.325 | 0.445 |
| 2 | TMPRSS4 | 0.716 | 0.5 | 0.568 |
| 2 | PI3 | 0.795 | 0.584 | 0.494 |
| 3 | CHP2 | 0.9 | 0.551 | 0.223 |
| 3 | ARG1 | 0.973 | 0.513 | 0.055 |
| 3 | LOR | 0.879 | 0.869 | 0.923 |
| 3 | PSORS1C2 | 0.923 | 0.492 | 0.152 |
| 4 | CD1B | 0.802 | 0.394 | 0.326 |
| 4 | GPR171 | 0.547 | 0.459 | 0.839 |
| 4 | CCL22 | 0.732 | 0.289 | 0.378 |
| 4 | CCL18_1 | 0.849 | 0.502 | 0.303 |
| 4 | COL6A6 | 0.43 | 0.176 | 0.692 |
| 4 | CCL18_2 | 0.792 | 0.456 | 0.383 |
| 5 | LCE2B | 0.908 | 0.503 | 0.185 |
| 5 | PGF | 0.819 | 0.514 | 0.373 |
| 5 | CTSL2 | 0.618 | 0.511 | 0.781 |
| 5 | MSMB_1 | 0.867 | 0.628 | 0.356 |
| 5 | LGR5 | 0.633 | 0.297 | 0.523 |
| 5 | CRCT1 | 0.906 | 0.554 | 0.21 |
| 5 | RNASE7_2 | 0.827 | 0.504 | 0.348 |
| 6 | S100A7 | 0.796 | 0.253 | 0.273 |
| 6 | CCL17 | 0.574 | 0.218 | 0.545 |
| 6 | SERPINB3_1 | 0.882 | 0.458 | 0.217 |
| 6 | SERPINB4 | 0.784 | 0.509 | 0.44 |
| 6 | GALNT6 | 0.609 | 0.29 | 0.552 |
| 7 | DIO2 | 0.77 | 0.279 | 0.319 |
| 7 | CARD18 | 0.77 | 0.214 | 0.292 |
| 8 | AQP9 | 0.744 | 0.264 | 0.347 |
| 8 | SERPINB3_2 | 0.829 | 0.419 | 0.294 |
| 8 | S100A8 | 0.622 | 0.404 | 0.635 |
| 8 | RNASE7_1 | 0.886 | 0.327 | 0.17 |
| 8 | RNASE7_3 | 0.94 | 0.447 | 0.109 |
| 8 | BTC_2 | 0.739 | 0.487 | 0.51 |
| 9 | HSD11B1 | 0.679 | 0.186 | 0.394 |
| 9 | RGS1 | 0.679 | 0.222 | 0.413 |
| 10 | RRM2 | 0.87 | 0.561 | 0.296 |
| 10 | GZMB | 0.586 | 0.41 | 0.701 |
| 10 | GPD1 | 0.708 | 0.223 | 0.376 |
| 10 | KYNU | 0.632 | 0.417 | 0.631 |
| 10 | TACC3 | 0.752 | 0.371 | 0.395 |
| 11 | OMD | 0.892 | 0.28 | 0.15 |
| 11 | BTC_1 | 0.892 | 0.333 | 0.162 |
| 12 | IL1F7_2 | 0.963 | 0.617 | 0.096 |
| 12 | OGN | 0.744 | 0.187 | 0.315 |
| 12 | SLC46A2 | 0.932 | 0.794 | 0.33 |
| 12 | IL1F7_1 | 0.988 | 0.602 | 0.03 |
| 13 | PSG7 | 0.843 | 0.276 | 0.216 |
| 13 | FADS1 | 0.744 | 0.637 | 0.705 |
| 13 | 1L27RA | 0.687 | 0.213 | 0.397 |

Table 14 shows regression modeling using representative genes as the predictor variables and the change in symptom score post-vs. pre-treatment as the outcome variable for pimecrolimus.

TABLE 14

Pimecrolimus outcome modeling glm(formula = SYM ~ FAR2 + LCE2B + RNASE7_2 + CCL18_1 + SERPINB3_1, data = PC eczema)

Deviance Residuals:

| 1 | 2 | 3 | 4 | 5 | 6 | 7 | 8 | 9 | 10 |
|---|---|---|---|---|---|---|---|---|---|
| −0.0758 | −0.7161 | 0.3274 | −4.1095 | −24.8403 | 24.1597 | −10.1988 | −0.0238 | 2.5452 | 12.9322 |

Coefficients:

|  | Estimate | Std. Error | t value | Pr(>|t|) |
|---|---|---|---|---|
| (Intercept) | −7.661 | 27.502 | −0.279 | 0.7944 |
| FAR2 | 37.842 | 11.493 | 3.293 | 0.0301* |
| LCE2B | −17.466 | 16.971 | −1.029 | 0.3616 |
| RNASE7_2 | 64.196 | 18.279 | 3.512 | 0.0246* |

TABLE 14-continued

| Pimecrolimus outcome modeling | | | | |
|---|---|---|---|---|
| CCL18_1 | −5.411 | 3.931 | −1.376 | 0.2407 |
| SERPINB3_1 | −136.799 | 33.501 | −4.083 | 0.0151* |

Signif. codes: 0 '*' 0.001 '' 0.01 '*' 0.05 '.' 0.1 ' ' 1
(Dispersion parameter for gaussian family taken to be 373.9955)
Null deviance: 10858 on 9 degrees of freedom
Residual deviance: 1496 on 4 degrees of freedom
AIC: 92.458
Number of Fisher Scoring iterations: 2

C. Dupilumab Drug Effect

Samples in Dupilumab dataset include GSE59294.

TABLE 15

Patient data for paired samples
(obtained from NCBI GEO gene expression database)

| Patient Number | EASI-PRE | EASI-POST | EASI-post/pre | NCBI GEO ID Of pre-treatment samples | NCBI GEO ID Of post-treatment samples | Dupilumab dose |
|---|---|---|---|---|---|---|
| 1 | 34.6 | 9.105 | 0.263 | GSM1432962 | GSM1432963 | 300 mg |
| 2 | 31.45 | 3.835 | 0.122 | GSM1432970 | GSM1432971 | 300 mg |
| 3 | 34.65 | 1.526 | 0.044 | GSM1432974 | GSM1432971 | 300 mg |

The fold-change (post-treatment/pre-treatment) of expression values of the ECZEMA55 member genes have been clustered using JMP® SAS® program. Paired punch biopsy samples collected before and after treatment have been used to identify post-vs. pre-treatment responses of dupilumab. The result shows that the responses of the ECZEMA55 member genes to dupilumab treatment can grouped into multiple correlated clustered, with each cluster predominantly represented by the post-vs. pre-treatment response of one predominant gene in the cluster. Dupilumab-response can be grouped into 8 clusters (FIG. 3). Clusters including most variables were taken for downstream regression analysis.

TABLE 16

ECZEMA55 member gene clustered behavior with dupilumab treatment Cluster Members

| Cluster | Members | Rsquare with Own Cluster | Rsquare with Next Closest | 1-Rsquare Ratio |
|---|---|---|---|---|
| 1 | ARK1B10 | 0.808 | 0.322 | 0.284 |
| 1 | ARG1 | 0.877 | 0.396 | 0.203 |
| 1 | CD1B | 0.848 | 0.364 | 0.239 |
| 1 | DIO2 | 0.587 | 0.33 | 0.617 |
| 1 | DKK2 | 0.839 | 0.476 | 0.307 |
| 1 | IL1F7_2 | 0.705 | 0.649 | 0.841 |
| 1 | IL27RA | 0.692 | 0.619 | 0.808 |
| 1 | KRT16 | 0.903 | 0.487 | 0.188 |
| 1 | NCAPG | 0.889 | 0.341 | 0.169 |
| 1 | PGF | 0.855 | 0.371 | 0.23 |
| 1 | PSOR1C2 | 0.802 | 0.263 | 0.269 |
| 1 | RGS1 | 0.792 | 0.597 | 0.516 |
| 1 | RNASE7_1 | 0.885 | 0.343 | 0.175 |
| 1 | RRM2 | 0.775 | 0.692 | 0.73 |
| 1 | S100A8 | 0.768 | 0.177 | 0.282 |
| 1 | SELE | 0.842 | 0.21 | 0.201 |
| 1 | TMPRSS4 | 0.856 | 0.341 | 0.219 |
| 2 | CCL17 | 0.771 | 0.524 | 0.481 |
| 2 | OGN | 0.867 | 0.37 | 0.21 |
| 2 | RNASE7_3 | 0.887 | 0.452 | 0.207 |
| 2 | TACC3 | 0.864 | 0.376 | 0.217 |
| 2 | TYMP | 0.897 | 0.616 | 0.268 |
| 3 | APOBEC3A | 0.973 | 0.428 | 0.047 |
| 3 | CARD18 | 0.863 | 0.202 | 0.172 |
| 3 | CCL18_1 | 0.841 | 0.21 | 0.202 |
| 3 | CCL22 | 0.829 | 0.285 | 0.24 |
| 3 | DEFB4A | 0.469 | 0.428 | 0.927 |
| 3 | GPR171 | 0.753 | 0.431 | 0.434 |
| 3 | RNASE7_2 | 0.481 | 0.192 | 0.642 |
| 4 | CCL18_2 | 0.754 | 0.284 | 0.343 |
| 4 | CRCT1 | 0.451 | 0.25 | 0.732 |
| 4 | FABP7 | 0.623 | 0.377 | 0.605 |
| 4 | GAL | 0.729 | 0.481 | 0.523 |
| 4 | GPD1 | 0.599 | 0.468 | 0.753 |
| 4 | GZMB | 0.851 | 0.228 | 0.192 |
| 4 | HSD11B1 | 0.82 | 0.598 | 0.447 |
| 4 | IL1F7_1 | 0.887 | 0.425 | 0.197 |
| 4 | LGR5 | 0.797 | 0.483 | 0.392 |
| 4 | LOR | 0.862 | 0.17 | 0.167 |
| 4 | PSG7 | 0.843 | 0.482 | 0.303 |
| 4 | S100A7 | 0.845 | 0.331 | 0.232 |
| 5 | CHP2 | 0.621 | 0.471 | 0.717 |
| 5 | GALNT6 | 0.907 | 0.521 | 0.194 |
| 5 | SERPINB3_1 | 0.744 | 0.343 | 0.39 |
| 5 | SERPINB4 | 0.73 | 0.185 | 0.331 |
| 6 | BTC_1 | 0.954 | 0.447 | 0.083 |
| 6 | FADS1 | 769 | 0.688 | 0.739 |
| 6 | LCE2B | 0.841 | 0.489 | 0.312 |
| 6 | MSMB_1 | 0.763 | 0.193 | 0.293 |
| 6 | MSMB_2 | 0.74 | 0.502 | 0.522 |
| 6 | OMD | 0.862 | 0.377 | 0.222 |
| 7 | AQP9 | 0.947 | 0.297 | 0.076 |
| 7 | COL6A6 | 0.66 | 0.475 | 0.648 |
| 7 | PI3 | 0.452 | 0.21 | 0.694 |
| 7 | SERPINB3_2 | 0.632 | 0.226 | 0.476 |
| 7 | SLC46A2 | 0.803 | 0.467 | 0.37 |
| 8 | BTC_2 | 0.933 | 0.494 | 0.132 |
| 8 | CTSL2 | 0.498 | 0.205 | 0.632 |
| 8 | FAR2 | 0.907 | 0.438 | 0.165 |

TABLE 16-continued

ECZEMA55 member gene clustered behavior with dupilumab treatment
Cluster Members

| Cluster | Members | Rsquare with Own Cluster | Rsquare with Next Closest | 1-Rsquare Ratio |
|---|---|---|---|---|
| 8 | HPGDS | 0.715 | 0.511 | 0.583 |
| 8 | KYNU | 0.875 | 0.688 | 0.402 |

TABLE 17

Regression model using representative genes as the predictor variables and the change in symptom score (post- vs. pre-treatment) as the outcome variable for dupilumab
lm(formula = SYM~NCAPG + LOR + APOBEC3A + BTC_1 + RNASE7_3 + AQP9, data = D upi)

Residuals:

| 1 | 2 | 3 | 4 | 5 | 6 | 7 | 8 |
|---|---|---|---|---|---|---|---|
| −0.0013786 | −0.0065001 | 0.0042012 | −0.0091326 | 0.0006803 | 0.0042787 | −0.0019159 | 0.0097670 |

Coefficients:

|  | Estimate | Std. Error | t value | Pr(>|t|) |
|---|---|---|---|---|
| (Intercept) | 2.30570 | 0.23388 | 9.859 | 0.0644 . |
| NCAPG | −0.22236 | 0.05924 | −3.754 | 0.1657 |
| LOR | −0.07479 | 0.04230 | −1.768 | 0.3277 |
| APOBEC3A | −0.69977 | 0.08790 | −7.961 | 0.0796 . |
| BTC_1 | 0.25087 | 0.06079 | 4.127 | 0.1513 |
| RNASE7_3 | −0.04606 | 0.03872 | −1.189 | 0.4451 |
| AQP9 | −1.34067 | 0.12555 | −10.678 | 0.0594 . |

Signif. codes: 0 '*' 0.001 '' 0.01 '*' 0.05 '.' 0.1 ' ' 1
Residual standard error: 0.01622 on 1 degrees of freedom
Multiple R-squared: 0.9935,
Adjusted R-squared: 0.9548
F-statistic: 25.64 on 6 and 1 DF,
p-value: 0.15

D. Including 'Pre-Treatment' Symptom Score (EASI-Pre) to Improve the Model:

Dupilumab is a fully humanized monoclonal IgG4 antibody that inhibits interleukin-4 (IL-4) and interleukin-13 (IL-13) signaling by specifically binding to the IL-4Rα subunit shared by the IL-4 and IL-13 receptor complexes. Dupilumab inhibits IL-4 signaling via the Type I receptor and both IL-4 and IL-13 signaling through the Type II receptor inhibiting IL-4 and IL-13 cytokine-induced responses, including the release of proinflammatory cytokines, chemokines and IgE. Contrary to the topical treatments (such as betamethasone and pimecrolimus), dupilumab is administered as a systemic treatment in the form of injections every alternate week and monitored for outcome.

It was posited that pre-treatment symptom score (which might have a significant impact on the treatment outcome, since more severe disease may take more sustained treatment to achieve significant outcome) may be added as an independent variable with gene expression changes in order to predict treatment outcome (i.e. post-treatment symptom score). We therefore added pre-treatment symptom score for analysis and for generating regression models FIG. 4 shows the ECZEMA55 treatments-responsive genes (variables) in each cluster along with the pre-treatment symptom score, most representative gene variable in the cluster along with Cluster Proportion of Variation Explained and Total Proportion of Variation Explained. Dupilumab-response can be grouped into 8 clusters. They are arranged by the number of member genes they contain.

TABLE 18

Cluster Summary
Cluster Members

| Cluster | Members | Rsquare with Own Cluster | Rsquare with Next Closest | 1-Rsquare Ratio |
|---|---|---|---|---|
| 1 | AKR1B10 | 0.815 | 0.322 | 0.273 |
| 1 | ARG1 | 0.872 | 0.451 | 0.232 |
| 1 | CD1B | 0.856 | 0.364 | 0.227 |

TABLE 18-continued

Cluster Summary
Cluster Members

| Cluster | Members | Rsquare with Own Cluster | Rsquare with Next Closest | 1-Rsquare Ratio |
|---|---|---|---|---|
| 1 | DIO2 | 0.572 | 0.488 | 0.837 |
| 1 | DKK2 | 0.831 | 0.583 | 0.407 |
| 1 | IL1F7_2 | 0.698 | 0.649 | 0.861 |
| 1 | IL27RA | 0.669 | 0.663 | 0.983 |
| 1 | KRT16 | 0.894 | 0.496 | 0.21 |
| 1 | NCAPG | 0.889 | 0.458 | 0.205 |
| 1 | PGF | 0.863 | 0.494 | 0.272 |
| 1 | PSOR1C2 | 0.81 | 0.343 | 0.289 |
| 1 | RGS1 | 0.802 | 0.597 | 0.491 |
| 1 | RNASE7_1 | 0.891 | 0.391 | 0.178 |
| 1 | S100A8 | 0.785 | 0.305 | 0.31 |
| 1 | SELE | 0.856 | 0.308 | 0.209 |
| 1 | TMPRSS4 | 0.86 | 0.47 | 0.264 |
| 2 | CCL17 | 0.771 | 0.524 | 0.481 |
| 2 | OGN | 0.867 | 0.37 | 0.21 |
| 2 | RNASE7_3 | 0.887 | 0.452 | 0.207 |
| 2 | TACC3 | 0.864 | 0.376 | 0.217 |
| 2 | TYMP | 0.897 | 0.616 | 0.268 |
| 3 | APOBEC3A | 0.959 | 0.428 | 0.072 |
| 3 | CARD18 | 0.886 | 0.241 | 0.15 |
| 3 | CCL18_1 | 0.863 | 0.27 | 0.187 |
| 3 | CCL22 | 0.824 | 0.29 | 0.247 |
| 3 | CHP2 | 0.571 | 0.441 | 0.767 |
| 3 | DEFB4A | 0.434 | 0.428 | 0.989 |
| 3 | GPR171 | 0.761 | 0.431 | 0.421 |
| 3 | RNASE7_2 | 0.431 | 0.2 | 0.711 |

TABLE 18-continued

Cluster Summary
Cluster Members

| Cluster | Members | Rsquare with Own Cluster | Rsquare with Next Closest | 1-Rsquare Ratio |
|---|---|---|---|---|
| 4 | CCL18_2 | 0.754 | 0.267 | 0.336 |
| 4 | CRCT1 | 0.451 | 0.25 | 0.732 |
| 4 | FABP7 | 0.623 | 0.377 | 0.605 |
| 4 | GAL | 0.729 | 0.475 | 0.517 |
| 4 | GPD1 | 0.599 | 0.462 | 0.745 |
| 4 | GZMB | 0.851 | 0.228 | 0.192 |
| 4 | HSD11B1 | 0.82 | 0.597 | 0.446 |
| 4 | IL1F7_1 | 0.887 | 0.425 | 0.197 |
| 4 | LGR5 | 0.797 | 0.483 | 0.392 |
| 4 | LOR | 0.862 | 0.168 | 0.166 |
| 4 | PSG7 | 0.843 | 0.482 | 0.303 |
| 4 | S100A7 | 0.845 | 0.331 | 0.232 |
| 5 | AQP9 | 0.95 | 0.297 | 0.071 |
| 5 | COL6A6 | 0.643 | 0.396 | 0.591 |
| 5 | PI3 | 0.494 | 0.21 | 0.641 |
| 5 | SERPINB3_2 | 0.621 | 0.226 | 0.49 |
| 5 | SLC46A2 | 0.732 | 0.467 | 0.502 |
| 5 | pre | 0.777 | 0.26 | 0.302 |
| 6 | GALNT6 | 0.951 | 0.496 | 0.096 |
| 6 | RRM2 | 0.82 | 0.746 | 0.707 |
| 6 | SERPINB3_1 | 0.761 | 0.343 | 0.363 |
| 6 | SERPINB4 | 0.706 | 0.169 | 0.354 |
| 7 | BTC_1 | 0.954 | 0.447 | 0.083 |
| 7 | FADS1 | 0.769 | 0.688 | 0.739 |
| 7 | LCE2B | 0.841 | 0.489 | 0.312 |
| 7 | MSMB_1 | 0.763 | 0.195 | 0.294 |
| 7 | MSMB_2 | 0.74 | 0.477 | 0.497 |
| 7 | OMD | 0.862 | 0.361 | 0.216 |
| 8 | BTC_2 | 0.933 | 0.433 | 0.117 |
| 8 | CTSL2 | 0.498 | 0.22 | 0.645 |
| 8 | FAR2 | 0.907 | 0.438 | 0.165 |
| 8 | HPGDS | 0.715 | 0.531 | 0.607 |
| 8 | KYNU | 0.875 | 0.688 | 0.402 |

TABLE 19

Regression model using representative genes as the predictor variables and the change in symptom score (post-vs. pre-treatment) as the outcome variable for dupilumab with pre-treatment symptom score as an additional predictor variable.

Call:
lm(formula = SYM ~ RNASE7_1 + LOR + APOBEC3A + BTC_1 + AQP9 + pre, data = Dupi)

Residuals:

| 1 | 2 | 3 | 4 | 5 | 6 | 7 | 8 |
|---|---|---|---|---|---|---|---|
| −0.052814 | −0.056810 | −0.006896 | 0.018378 | 0.021305 | 0.047533 | −0.016515 | 0.045819 |

Coefficients:

|  | Estimate | Std. Error | t value | Pr(>|t|) |
|---|---|---|---|---|
| (Intercept) | 73.443336 | 1.489812 | 49.297 | 0.0129* |
| RNASE7_1 | −1.768774 | 0.286490 | −6.174 | 0.1022 |
| LOR | −0.854073 | 0.360257 | −2.371 | 0.2541 |
| APOBEC3A | −19.702912 | 0.529151 | −37.235 | 0.0171* |
| BTC_1 | 5.168149 | 0.206195 | 25.064 | 0.0254* |
| AQP9 | −51.019661 | 1.435734 | −35.536 | 0.0179* |
| pre | 0.048885 | 0.008585 | 5.694 | 0.1107 |

Signif. codes: 0 '*' 0.001 '' 0.01 '*' 0.05 '.' 0.1 ' ' 1
Residual standard error: 0.1072 on 1 degrees of freedom
Multiple R-squared: 0.9999, Adjusted R-squared: 0.999
F-statistic: 1128 on 6 and 1 DF,
p-value: 0.02278

Example 4. Application of ECZEMA55 Gene Panel to Classify Skin Samples Subjected to Narrow Band UVB Therapy Narrow band UVB has been shown to be effective in controlling AD symptoms. Gene expression data of pre- and post-treatment samples have been downloaded from the NCBI GEO. The relevant dataset identifier is GSE27887, which is publicly available. The dataset contains data obtained from 18 samples, of which 8 samples are paired (Table 20).

TABLE 20

Dataset Pairs

|  | P1 | P2 | P3 | P4 | P5 | P6 | P7 | P8 | P9 | P10 |
|---|---|---|---|---|---|---|---|---|---|---|
| PRE | P1-pre | P2-pre | P3-pre | P4-pre | P5-pre | P6-pre | P7-pre | P8-pre | NA | P10-pre |

TABLE 20-continued

| | Dataset Pairs | | | | | | | | | |
|---|---|---|---|---|---|---|---|---|---|---|
| | P1 | P2 | P3 | P4 | P5 | P6 | P7 | P8 | P9 | P10 |
| POST | P1-post | P2-post | P3-post | P4-post | NA | P6-post | P7-post | P8-post | P9-post | P10-post |

Figure 5:
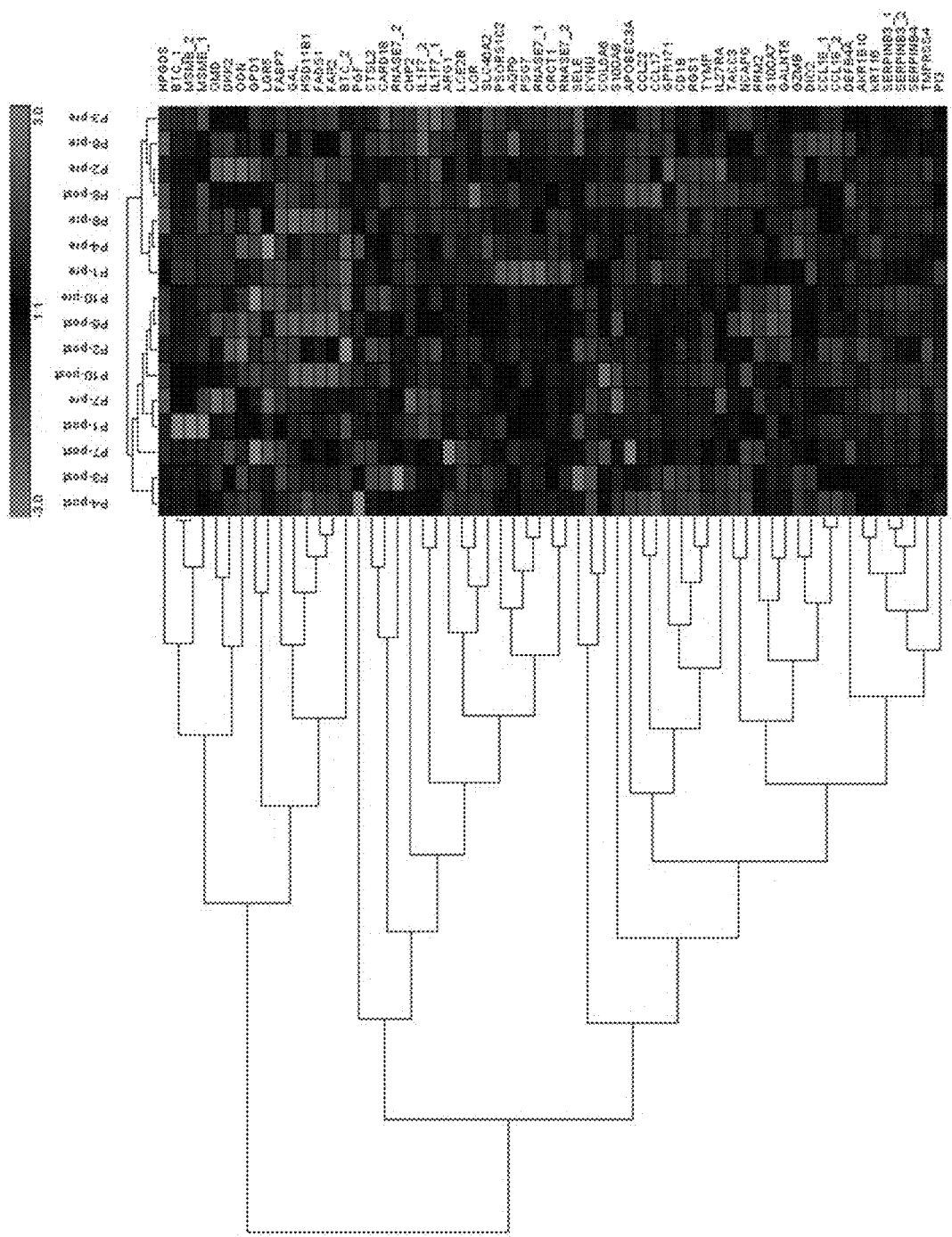
FIG. 5 shows a heatmap of pre- and post-treatment gene expression data from P1, P2, P3, P4, P6, P7, P8, and P10 subjects. Data was clustered by genes and by samples. GENESIS program used to process data. Results show data can be clustered into two clusters containing 9 samples and 7 samples, respectively, with a mis-classification rate of 12.5%.

Pre- and post-treatment gene expression data from P1, P2, P3, P4, P6, P7, P8 and P10 subjects was used to produce a heatmap (FIG. 5). The data was clustered by genes and by samples, Program GENESIS was used to process the data.

The results show that data can be separated into two clusters containing 9 samples (1 pre- and 8 post-treatment samples) and 7 samples (1 post- and 6 pre-treatment samples) respectively with a mis-classification rate of 12.5%.

Example 5. ECZEMA55 Gene Panel Members

FIG. 6 is a table showing expression of members of the ECZEMA55 gene panel compared to normal skin. Expression changes are due to different treatment options. Betamethasone, pimecrolimus, and dupilumab are shown. Note direction and magnitude of treatment-related expression change for each gene. Treatment inducing change in a direction opposite to that occurring in ECZEMA55 can drive treatment-associated health benefits.

Example 6. Diagnosis and Treatment of a Patient Suffering from AD

A patient comes to the clinic with itchy, inflamed skin lesions. The clinician suspects atopic dermatitis. The symptoms flare periodically and may have a phenotype overlapping with other diseases. The diagnosis is incomplete by visual assessment.

Skin biopsy is performed using a minimally invasive disposable punch. The skin biopsy site is swabbed with isopropyl alcohol (70%) and anesthetized with local anesthetic (1 mL of 1% lidocaine+adrenaline). Using a punch biopsy needle, a 4 mm² full thickness skin biopsy from the lesion is obtained and stored in RNA later solution and sent to a diagnostic lab to perform RT-PCR assay.

RNA is isolated from the tissue and subjected to quantitative RT-PCR to compare the levels of expression of the 89ADGES genes of this tissue to normal healthy skin. Five pre-collected RNA samples obtained from healthy normal skin stored at −80° C. are used as controls in the assay. The result generates a list of 89-member genes that are either up-regulated or down-regulated in the suspected AD sample. The directions of changes are similar to those expected in AD (i.e., similar to or concordant with Table 3). For example, SERPINB, S100A7, CCL18, CD1B, CCL17 are up-regulated about 6, 6, 4, 4, 2 and 2 times, while LCE2B, BTC, FADS1, LOR, MSMB are down-regulated 3.0, 3.0, 2.5, 2.5 and 2 times. At least 25% gene expression changes are required to designate the sample as AD skin. In this case, more than 50 genes out of 89 total AD-relevant are differentially regulated (>2 times up- or down-regulated, which designates the samples as collected from an AD patient. The patient is referred for AD therapy.

The clinician observes that SERPINB4 gene is a top differentially regulated gene in the patient. As betamethasone can reverse the disease-related change for SERPINB4 (see Table 21, ECZEMA55 and AD Treatment), compared to pimecrolimus, the patient is advised to apply betamethasone ointment.

Example 7. Managing Treatment of a Patient Suffering from AD

An AD patient comes to the clinic with severe itch and lesions on at least 45% of his body surface. Symptoms indicate a possible diagnosis of atopic dermatitis. He is not sufficiently controlled by topical treatments like pimecrolimus and betamethasone. The patient is advised to begin dupilumab treatment. Duplimumab is administered by subcutaneous injection at recommended dosing for adult patients, which is initially at a dose of 600 mg, followed by 300 mg administered every two weeks. The patient is given one 600 mg injection followed by two 300 mg injections over the course of 4 weeks. Pre- and post-treatment samples are collected and stored in RNA later solution (Invitrogen) at −80° C.

Pre- and post-treatment skin biopsy is performed using a minimally invasive disposable punch. The skin biopsy site is swabbed with isopropyl alcohol (70%) and anesthetized with local anesthetic (1 mL of 1% lidocaine+adrenaline). Using a punch biopsy needle, a 4 mm² full thickness skin biopsy from the lesion is obtained and stored in RNA later solution and sent to the diagnostic lab to perform RT-PCR assay.

RNA is isolated from the tissue and subjected to quantitative RT-PCR to compare the levels of expression of the ECZEMA55 genes of the patient's tissue to normal healthy skin. Expression of about 30 of the genes are changed compared to pre-treatment. The direction of change is opposite to gene expression in AD disease state compared to healthy skin. The treatment is assessed as effective and the patient is advised to receive further dupilumab treatment doses.

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

We claim:

1. A method of diagnosing and treating a subject suffering from atopic dermatitis (AD), the method comprising:
   (a) obtaining a skin biopsy from a subject suspected of suffering from AD;
   (b) determining a level of RNA expression in the skin biopsy of a plurality of genes comprising SERPINB4, AKR1B10, SERPINB3, S100A7, DEFB4A, RRM2, CCL18, PI3, COL6A6, KRT16, CCL22, NCAPG, TMPRSS4, KRT6, SELE, GALNT6, PGF, CCL17, APOBEC3A, CBLC, CD1B, IGL, CDSN, BTC, C1orf46, C1orf68, ASPRV1, PSOR1C2, IL1F7, POF1B, LOR, SLURP1, MSMB, CST6, ELMODJ, FABP7, CARD18, CTSL2, GREM1, GPLD1, HBA, ARG1, ANXA9, DKK2, KLK5, LYVE1, PSG7, AQP9, CPA3, GPD1, HSD11B1, ARHGAP18, EREG, CLDN23, FLG, SCEL, and CHP2;
   (c) comparing said determined level of RNA expression of the plurality of genes to the level of expression of the plurality of genes in a reference sample comprising RNA expression products from normal healthy skin cells;
   (d) diagnosing the subject as suffering from AD when SERPINB4, AKR1B10, SERPINB3, S100A7, DEFB4A, RR1112, CCL18, PI3, COL6A6, KRT16, CCL22, NCAPG, TMPRSS4, KRT6, SELE, GALNT6, PGF, CCL17, APOBEC3A, CBLC, CD1B, and IGL are up-regulated compared to the reference sample and when CDSN, BTC, C1orf46, C1orf68, ASPRV1, PSOR1C2, IL1F7, POF1B, LOR, SLURP1, MSMB, CST6, ELMOD1, FABP7, CARD18, CTSL2, GREM1, GPLD1, HBA, ARG1, ANXA9, DKK2, KLK5, LYVE1, PSG7, AQP9, CPA3, GPD1, HSD11B1, IGJ, ARHGAP18, EREG, CLDN23, FLG, SCEL, and CHP2 are down-regulated compared to the reference sample; and
   (e) treating the diagnosed subject with one or more therapeutic agents selected from the group consisting of corticosteroids, betamethasone, tacrolimus, pimecrolimus, narrow-band UVB, PDE4 inhibitors, tofacitinib, dupilumab, and nemolizumab.

2. The method of claim 1, wherein determining RNA expression levels comprises molecular methods selected from the group consisting of quantitative RT-PCR, microarray, and RNA-seq.

3. The method of claim 1, wherein determining a level of RNA expression in the skin biopsy comprises:
   (a) isolating RNA from the skin biopsy;
   (b) using the isolated RNA to create cRNA;
   (c) labeling the cRNA with a fluorescent dye; and
   (d) hybridizing the labeled cRNA to a microarray.

4. A method of diagnosing and treating a subject suffering from atopic dermatitis (AD), the method comprising:
   (a) obtaining a skin biopsy from a subject suspected of suffering from AD;
   (b) generating a skin biopsy transcriptional profile comprising RNA expression levels of a plurality of genes comprising SERPINB4, AKR1B10, SERPINB3, S100A7, DEFB4A, RRM2, CCL18, PI3, COL6A6, KRT16, CCL22, NCAPG, TMPRSS4, KRT6, SELE, GALNT6, PGF, CCL17, APOBEC3A, CBLC, CD1B, IGL, CDSN, BTC, C1orf46, C1orf68, ASPRV1, PSOR1C2, IL1F7, POF1B, LOR, SLURP1, MSMB, CST6, ELMODJ, FABP7, CARD18, CTSL2, GREM1, GPLD1, HBA, ARG1, ANXA9, DKK2, KLK5, LYVE1, PSG7, AQP9, CPA3, GPD1, HSD11B1, IGJ, ARHGAP18, EREG, CLDN23, FLG, SCEL, and CHP2;
   (c) comparing the skin biopsy transcriptional profile to an AD signature transcriptional profile of the plurality of genes;
   (d) diagnosing the subject as suffering from AD when the skin biopsy transcriptional profile and the AD signature transcriptional profile are at least 25% concordant; and
   (e) treating the diagnosed subject with one or more therapeutic agents selected from the group consisting of corticosteroids, betamethasone, tacrolimus, pimecrolimus, narrow-band UVB, PDE4 inhibitors, tofacitinib, dupilumab, and nemolizumab.

5. The method of claim 4, wherein generating a skin biopsy transcriptional profile comprises:
   (a) determining RNA expression levels in the skin biopsy for the selected genes; and
   (b) comparing the RNA expression levels of the selected genes in the skin biopsy to control RNA expression levels from normal healthy skin cells to generate the skin biopsy transcriptional profile.

6. The method of claim 4, wherein determining RNA expression levels comprises molecular methods selected from the group consisting of quantitative RT-PCR, microarray, and RNA-seq.

7. The method of claim 4, wherein determining RNA expression levels in the skin biopsy comprises:
(a) isolating RNA from the skin biopsy;
(b) using the isolated RNA to create cRNA;
(c) labeling the cRNA with a fluorescent dye; and
(d) hybridizing the labeled cRNA to a microarray.

8. The method of claim 1, wherein determining the level of RNA expression in the skin biopsy of the plurality of genes of step (b) further comprises determining the level of RNA expression of one or more of S100A8, RGS1, KYNU, TYMP, IL27RA, GPR171, GZMB, EHBP1L1, TACC3, LCE2B, FADS1, CRCT1, SERPINB7, RNASE7, GAL, SLC46A2, HBB, CORIN, SCGB2A1, OGN, LOC100130476, LGR5, C15orf48, FAR2, HPGDS, SLIT2, SFRP2, MUC15, OMD, LOX, or DIO2; and
wherein step (d) further comprises diagnosing the subject as suffering from AD when one or more of S100A8, RGS1, KYNU, TYMP, IL27RA, GPR171, GZMB, EHBPIL1, or TACC3 is upregulated compared to the reference sample; and/or diagnosing the subject as suffering from AD when one or more of LCE2B, FADS1, CRCT1, SERPINB7, RNASE7, GAL, SLC46A2, HBB, CORIN, SCGB2A1, OGN, LOC100130476, LGR5, C15orf48, FAR2, HPGDS, SLIT2, SFRP2, MUC15, OMD, LOX or DIO2 is down-regulated compared to the reference sample.

9. The method of claim 4, wherein the plurality of genes further comprises one or more of S100A8, RGS1, KYNU, TYMP, IL27RA, GPR171, GZMB, EHBPIL1, TACC3, LCE2B, FADS1, CRCT1, SERPINB7, RNASE7, GAL, SLC46A2, HBB, CORIN, SCGB2A1, OGN, LOC100130476, LGR5, C15orf48, FAR2, HPGDS, SLIT2, SFRP2, MUC15, OMD, LOX, or DIO2.

* * * * *

UNITED STATES PATENT AND TRADEMARK OFFICE
CERTIFICATE OF CORRECTION

| | |
|---|---|
| PATENT NO. | : 11,376,261 B2 |
| APPLICATION NO. | : 16/224143 |
| DATED | : July 5, 2022 |
| INVENTOR(S) | : Debajyoti Ghosh, Tesfaye Mersha and Jonathan A. Bernstein |

It is certified that error appears in the above-identified patent and that said Letters Patent is hereby corrected as shown below:

In the Specification

In Column 2, Line(s) 47, delete "T4CC3" and insert --TACC3--, therefor.

In Column 2, Line(s) 54, after "GREM1", insert --,--.

In Column 2, Line(s) 58, after "LOX", insert --,--.

In Column 3, Line(s) 8, delete "FADS" and insert --FADS1--, therefor.

In Column 6, Line(s) 52, delete "PI13" and insert --PI3--, therefor.

In Column 7, Line(s) 32, delete "COL6A46" and insert --COL6A6--, therefor.

In Column 13, Line(s) 34, delete "fimigatus" and insert --fumigatus--, therefor.

In Column 18, Line(s) 18, after "regulated", delete "." and insert --,--, therefor.

In the Claims

In Column 37, Line(s) 35, Claim 1, delete "ELMODJ" and insert --ELMOD1--, therefor.

In Column 37, Line(s) 38, Claim 1, after "HSD11B1,", insert --IGJ,--.

In Column 37, Line(s) 47, Claim 1, delete "RR1112" and insert --RRM2--, therefor.

In Column 38, Line(s) 41, Claim 4, delete "ELMODJ" and insert --ELMOD1--, therefor.

Signed and Sealed this
Tenth Day of January, 2023

*Katherine Kelly Vidal*
Katherine Kelly Vidal
*Director of the United States Patent and Trademark Office*

SEQUENCE LISTING

<160> NUMBER OF SEQ ID NOS: 18

<210> SEQ ID NO 1
<211> LENGTH: 20
<212> TYPE: DNA
<213> ORGANISM: Mus musculus

<400> SEQUENCE: 1
tgccgaggat ttggaaaaag                                                     20

<210> SEQ ID NO 2
<211> LENGTH: 18
<212> TYPE: DNA
<213> ORGANISM: Mus musculus

<400> SEQUENCE: 2 cccccttga gcacacag                                                        18

<210> SEQ ID NO 3
<211> LENGTH: 20
<212> TYPE: DNA
<213> ORGANISM: Mus musculus

<400> SEQUENCE: 3
ccatgccctc tacaagaatg                                                     20

<210> SEQ ID NO 4
<211> LENGTH: 20
<212> TYPE: DNA
<213> ORGANISM: Mus musculus

<400> SEQUENCE: 4
atcaccatcg caaggaactc                                                     20

<210> SEQ ID NO 5
<211> LENGTH: 22
<212> TYPE: DNA
<213> ORGANISM: Mus musculus

<400> SEQUENCE: 5
cagatgatga aacaaaacat cg                                                  22

<210> SEQ ID NO 6
<211> LENGTH: 21
<212> TYPE: DNA
<213> ORGANISM: Mus musculus

<400> SEQUENCE: 6
agaccttgag tgctgctcat a                                                   21

<210> SEQ ID NO 7
<211> LENGTH: 17
<212> TYPE: DNA
<213> ORGANISM: Mus musculus

<400> SEQUENCE: 7
aacctgcaag ctgctat                                                        17

<210> SEQ ID NO 8
<211> LENGTH: 24
<212> TYPE: DNA
<213> ORGANISM: Mus musculus

<400> SEQUENCE: 8
cttgacattc atgagttcct ggta                                          24

<210> SEQ ID NO 9
<211> LENGTH: 21
<212> TYPE: DNA
<213> ORGANISM: Mus musculus

<400> SEQUENCE: 9
agaaaagaag acagccacct c                                             21

<210> SEQ ID NO 10
<211> LENGTH: 22
<212> TYPE: DNA
<213> ORGANISM: Mus musculus

<400> SEQUENCE: 10
cagaagttca agtcaccctc ag                                            22

<210> SEQ ID NO 11
<211> LENGTH: 26
<212> TYPE: DNA
<213> ORGANISM: Mus musculus

<400> SEQUENCE: 11
gatccattac cttctcttca catttc                                        26

<210> SEQ ID NO 12
<211> LENGTH: 23
<212> TYPE: DNA
<213> ORGANISM: Mus musculus

<400> SEQUENCE: 12
ctccattggt catgcatgtt att                                           23

<210> SEQ ID NO 13
<211> LENGTH: 19
<212> TYPE: DNA
<213> ORGANISM: Mus musculus

<400> SEQUENCE: 13
cttcttgctg tggcaattc                                                19

<210> SEQ ID NO 14
<211> LENGTH: 17
<212> TYPE: DNA
<213> ORGANISM: Mus musculus

<400> SEQUENCE: 14
tgatggcaga gggtgac                                                  17

<210> SEQ ID NO 15
<211> LENGTH: 20
<212> TYPE: DNA
<213> ORGANISM: Mus musculus

<400> SEQUENCE: 15
acatcagcat cacctccttc                                               20

<210> SEQ ID NO 16
<211> LENGTH: 19
<212> TYPE: DNA
<213> ORGANISM: Mus musculus

```
-continued

<400> SEQUENCE: 16
tctttccaca acccacagg                                              19

<210> SEQ ID NO 17
<211> LENGTH: 20
<212> TYPE: DNA
<213> ORGANISM: Mus musculus

<400> SEQUENCE: 17
agcgacagcc tctactactt                                             20

<210> SEQ ID NO 18
<211> LENGTH: 20
<212> TYPE: DNA
<213> ORGANISM: Mus musculus

<400> SEQUENCE: 18
cggcactctg tgctttctat                                             20
```